United States Patent
Hannon et al.

(10) Patent No.: US 11,534,573 B2
(45) Date of Patent: Dec. 27, 2022

(54) FLIP OPEN CATHETER PACKAGE

(71) Applicant: Hollister Incorporated, Libertyville, IL (US)

(72) Inventors: David Hannon, Ballina (IE); Martin McMenamin, Lifford (IE); Adam J. Foley, Swords (IE); Padraig M. O'Flynn, Ballina (IE); Stephen Collum, Castlebar (IE); Enda F. Carter, Galway (IE); Paul C. Fletter, Mt. Prospect, IL (US); Marine V. Richard, Carrieres sur Seine (FR); Daniel E. O'Brien, Calry (IE); Vincent Naughton, Sligo (IE)

(73) Assignee: Hollister Incorporated, Libertyville, IL (US)

(*) Notice: Subject to any disclaimer, the term of this patent is extended or adjusted under 35 U.S.C. 154(b) by 216 days.

(21) Appl. No.: 16/773,649

(22) Filed: Jan. 27, 2020

(65) Prior Publication Data
US 2020/0155796 A1 May 21, 2020

Related U.S. Application Data

(62) Division of application No. 15/314,436, filed as application No. PCT/US2015/033344 on May 29, 2015, now Pat. No. 10,561,817.
(Continued)

(51) Int. Cl.
*A61M 25/00* (2006.01)
*B65D 47/14* (2006.01)
(Continued)

(52) U.S. Cl.
CPC ...... *A61M 25/002* (2013.01); *A61M 25/0017* (2013.01); *A61M 25/0097* (2013.01);
(Continued)

(58) Field of Classification Search
CPC ............ A61M 25/002; A61M 25/0017; A61M 25/0097; A61M 2205/586; A61M 27/00; B65D 47/141; B65D 55/16; B65D 84/22
(Continued)

(56) References Cited

U.S. PATENT DOCUMENTS 3,203,545 A * 8/1965 Grossman .............. A61B 50/30
                                                422/291
3,369,542 A 2/1968 Thaidigsman
(Continued)

FOREIGN PATENT DOCUMENTS

AT        369994 B    2/1983
CN      2078634 U    6/1991
(Continued)

OTHER PUBLICATIONS

Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31.
(Continued)

*Primary Examiner* — Chun Hoi Cheung
(74) *Attorney, Agent, or Firm* — Cook Alex Ltd.

(57) ABSTRACT

A catheter package includes an elongated case. A cap is attached to the case by a flexible strap. The case receives the tubing portion of a catheter. The catheter has a funnel attached to the tubing. The funnel has a seal portion releasably engageable with the case. The cap is releasably engageable with the funnel to retain the funnel in contact with the case. A user can flip the cap off the funnel to permit removal of the catheter from the case. The funnel may include ridges or a tactile ring to improve the user's grip on the funnel. An adaptor may be disposed between the funnel and case to allow mating of different cross sectional shapes of the funnel and case. A hydration device may be inserted in the case.
(Continued)

Alternately, a tubular liner may be inserted in the case to separate liquid water on the outside of the liner from the catheter tubing on the inside of the liner. A window in the liner mounts a patch of filter material that permits the passage of water vapor into the interior of the liner.

20 Claims, 25 Drawing Sheets

Related U.S. Application Data

(60) Provisional application No. 62/005,635, filed on May 30, 2014.

(51) Int. Cl.
  *B65D 55/16* (2006.01)
  *B65D 81/22* (2006.01)
  *A61M 27/00* (2006.01)

(52) U.S. Cl.
  CPC ........... *B65D 47/141* (2013.01); *B65D 55/16* (2013.01); *B65D 81/22* (2013.01); *A61M 27/00* (2013.01); *A61M 2205/586* (2013.01)

(58) Field of Classification Search
  USPC ........ 206/571, 364, 210; 604/265, 171, 172, 604/263
  See application file for complete search history.

(56) References Cited

U.S. PATENT DOCUMENTS

| | | | |
|---|---|---|---|
| 3,854,483 A | 12/1974 | Powers | |
| 3,867,945 A | 2/1975 | Long | |
| 3,894,540 A | 7/1975 | Bonner, Jr. | |
| 3,920,023 A | 11/1975 | Dye | |
| 3,934,722 A | 1/1976 | Goldberg | |
| 4,043,345 A | 8/1977 | Kramann et al. | |
| 4,109,659 A | 8/1978 | Sheridan | |
| 4,248,214 A | 2/1981 | Hannah | |
| 4,432,758 A | 2/1984 | Finegold | |
| 4,553,959 A | 11/1985 | Hickey | |
| 4,684,369 A | 8/1987 | Wildemeersch | |
| 4,773,901 A | 9/1988 | Norton | |
| 4,921,096 A | 5/1990 | McFarlane | |
| 4,935,017 A | 6/1990 | Sylvanowicz | |
| 4,956,298 A | 9/1990 | Diekmann | |
| 5,084,036 A | 1/1992 | Rosenbaum | |
| 5,149,326 A | 9/1992 | Woodgrift et al. | |
| 5,217,114 A | 6/1993 | Gadberry et al. | |
| 5,225,165 A | 7/1993 | Perlman | |
| 5,380,270 A | 1/1995 | Ahmadzadeh | |
| 5,413,561 A | 5/1995 | Fischell et al. | |
| 5,417,326 A | 5/1995 | Winer | |
| 5,582,599 A | 12/1996 | Daneshvar | |
| 5,868,265 A | 2/1999 | Kobayashi | |
| 5,881,774 A | 3/1999 | Utterberg | |
| 5,919,170 A | 7/1999 | Woessner | |
| 6,258,078 B1 | 7/2001 | Thilly | |
| 6,585,721 B2 | 7/2003 | Fiore | |
| 6,822,253 B1 | 11/2004 | Martin et al. | |
| 6,908,013 B2 | 6/2005 | Thomson et al. | |
| 6,926,708 B1 | 8/2005 | Franks-Farah et al. | |
| 6,964,336 B2 * | 11/2005 | Harrold .............. | A61B 10/0051 206/363 |
| 7,120,487 B2 | 10/2006 | Nelson | |
| 7,438,704 B1 | 10/2008 | Kawashima et al. | |
| 7,546,931 B2 | 6/2009 | Giusti | |
| 7,571,804 B2 | 8/2009 | Kjellmann Bruun et al. | |
| 7,717,284 B2 | 5/2010 | Giusti | |
| 7,748,550 B2 | 7/2010 | Cho | |
| 7,867,220 B2 | 1/2011 | Tanghoj | |
| 7,886,907 B2 | 2/2011 | Murray et al. | |
| 7,967,744 B2 | 6/2011 | Kaye et al. | |
| 8,137,309 B2 | 3/2012 | Nishtala et al. | |
| 8,172,101 B2 | 5/2012 | Giusti | |
| 8,181,778 B1 | 5/2012 | van Groningen et al. | |
| 8,230,993 B2 | 7/2012 | Tanghoej | |
| 8,282,624 B2 | 10/2012 | Tanghoej et al. | |
| 8,361,057 B2 | 1/2013 | Tanghoej et al. | |
| 8,398,615 B2 | 3/2013 | Torstensen et al. | |
| 8,434,639 B2 | 5/2013 | Markert | |
| 8,439,213 B2 | 5/2013 | Goria et al. | |
| 8,448,798 B2 | 5/2013 | Groubert | |
| 8,491,568 B2 | 7/2013 | Schertiger et al. | |
| 8,529,549 B2 | 9/2013 | Tanghoj | |
| 8,579,115 B2 | 11/2013 | Murphy et al. | |
| 8,752,722 B2 | 6/2014 | Kuhn et al. | |
| 8,863,968 B2 | 10/2014 | Giusti | |
| 9,352,318 B2 | 5/2016 | Giusti | |
| 9,422,089 B2 | 8/2016 | Wheeler | |
| 11,020,561 B2 * | 6/2021 | O'Brien .............. | A61M 25/002 |
| 2003/0004496 A1 | 1/2003 | Tanghoj | |
| 2003/0060807 A1 | 3/2003 | Tanghoj | |
| 2005/0043715 A1 * | 2/2005 | Nestenborg .......... | A61M 25/002 206/439 |
| 2005/0137582 A1 * | 6/2005 | Kull-Osterlin ........ | A61L 29/085 206/571 |
| 2006/0116661 A1 | 6/2006 | Tanghoj | |
| 2006/0142737 A1 | 6/2006 | Tanghoj | |
| 2006/0180585 A1 | 8/2006 | Cunningham et al. | |
| 2008/0033371 A1 | 2/2008 | Updegraff et al. | |
| 2008/0289984 A1 | 11/2008 | Raven | |
| 2009/0054876 A1 | 2/2009 | Borodulin | |
| 2009/0166361 A1 | 7/2009 | Lourenco | |
| 2010/0087801 A1 * | 4/2010 | Torstensen .......... | A61M 25/002 206/364 |
| 2010/0106236 A1 | 4/2010 | Nelson | |
| 2010/0211050 A1 | 8/2010 | Luther | |
| 2010/0256580 A1 | 10/2010 | Faber | |
| 2010/0324540 A1 | 12/2010 | Paulen et al. | |
| 2011/0060317 A1 | 3/2011 | Frojd | |
| 2011/0224653 A1 | 9/2011 | Torstensen | |
| 2012/0016318 A1 | 1/2012 | Hoang et al. | |
| 2012/0165791 A1 | 6/2012 | Lovmar | |
| 2012/0179144 A1 | 7/2012 | Carleo | |
| 2012/0271281 A1 | 10/2012 | Schertiger | |
| 2013/0068767 A1 | 3/2013 | Fraser et al. | |
| 2013/0134123 A1 | 5/2013 | Fraser | |
| 2013/0161344 A1 | 6/2013 | Park et al. | |
| 2013/0218136 A1 | 8/2013 | Tanghoej et al. | |
| 2013/0261608 A1 | 10/2013 | Tanghoj | |
| 2013/0289537 A1 | 10/2013 | Schertiger | |
| 2013/0292286 A1 | 11/2013 | Van Groningen | |
| 2013/0327664 A1 | 12/2013 | Tanghoj | |
| 2014/0262860 A1 | 9/2014 | Hagel | |
| 2014/0263436 A1 | 9/2014 | Gelov et al. | |
| 2014/0360896 A1 | 12/2014 | Torstensen | |
| 2016/0016703 A1 | 1/2016 | Muhlemann | |
| 2016/0023818 A1 | 1/2016 | Gelov et al. | |
| 2016/0059999 A1 | 3/2016 | Fraser et al. | |
| 2016/0228872 A1 | 8/2016 | Giusti | |
| 2019/0358435 A1 * | 11/2019 | Andersin .......... | A61M 25/0009 |

FOREIGN PATENT DOCUMENTS

| | | |
|---|---|---|
| DE | 20117438 U1 | 3/2002 |
| DE | 10213411 A1 | 10/2003 |
| DE | 20317135 U1 | 2/2004 |
| DE | 202005008071 U1 | 7/2005 |
| DE | 202005009946 U1 | 9/2005 |
| DE | 202006013663 U1 | 11/2006 |
| DE | 202010006267 U1 | 11/2010 |
| DE | 202010007433 U1 | 7/2011 |
| DE | 202011107025 | 3/2013 |
| DE | 202011107059 | 3/2013 |
| DE | 102013014483 A1 | 6/2014 |
| EP | 0041487 A | 12/1981 |
| EP | 0134630 A | 3/1985 |
| EP | 0861639 A2 | 9/1998 |
| EP | 0996542 A1 | 5/2000 |
| EP | 1466645 A2 | 10/2004 |

(56) References Cited

FOREIGN PATENT DOCUMENTS

| | | |
|---|---|---|
| EP | 1392575 B1 | 9/2005 |
| EP | 1593710 A1 | 11/2005 |
| EP | 1634554 A2 | 3/2006 |
| EP | 1638856 A1 | 3/2006 |
| EP | 1671663 A1 | 6/2006 |
| EP | 1878461 A1 | 1/2008 |
| EP | 1897579 A1 | 3/2008 |
| EP | 1897580 A1 | 3/2008 |
| EP | 1982741 A2 | 10/2008 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2295108 | 3/2011 |
| EP | 2468319 A1 | 6/2012 |
| EP | 2504054 A1 | 10/2012 |
| EP | 2515985 A1 | 10/2012 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2682069 A1 | 1/2014 |
| EP | 2686054 A1 | 1/2014 |
| EP | 2774648 A1 | 9/2014 |
| EP | 2576374 B1 | 9/2016 |
| FR | 2717676 A1 | 9/1995 |
| GB | 2031735 A | 4/1980 |
| GB | 2033231 A | 5/1980 |
| GB | 2322079 A | 8/1998 |
| JP | 2001025473 | 1/2001 |
| KR | 20110101674 | 7/2012 |
| WO | WO 9608219 A1 | 3/1996 |
| WO | WO 9726937 A1 | 7/1997 |
| WO | WO 9741811 A1 | 11/1997 |
| WO | WO 9811932 A1 | 3/1998 |
| WO | WO 9819729 A1 | 5/1998 |
| WO | WO 9930761 A1 | 6/1999 |
| WO | WO 9942155 A2 | 8/1999 |
| WO | WO 0016843 A1 | 3/2000 |
| WO | WO 0030575 A1 | 6/2000 |
| WO | WO 0047494 A1 | 8/2000 |
| WO | WO 0143807 A1 | 6/2001 |
| WO | WO 0160255 A1 | 8/2001 |
| WO | WO 02060361 A2 | 8/2002 |
| WO | WO 02080843 A2 | 10/2002 |
| WO | WO 03001994 A1 | 1/2003 |
| WO | WO 03008028 A2 | 1/2003 |
| WO | WO 03008029 A2 | 1/2003 |
| WO | WO 03022561 A1 | 3/2003 |
| WO | WO 03045487 A2 | 6/2003 |
| WO | WO 03061732 A2 | 7/2003 |
| WO | WO 03092779 A1 | 11/2003 |
| WO | WO 03097237 A2 | 11/2003 |
| WO | WO 2004/021890 A1 | 3/2004 |
| WO | WO 2004/032750 A1 | 4/2004 |
| WO | WO 2004/035123 A1 | 4/2004 |
| WO | WO 2004/050155 A1 | 6/2004 |
| WO | WO 2004/054446 A1 | 7/2004 |
| WO | WO 2004/054653 | 7/2004 |
| WO | WO 2004/056414 | 7/2004 |
| WO | WO 2004/103153 A2 | 12/2004 |
| WO | WO 2005/003725 A2 | 1/2005 |
| WO | WO 2005/004964 A1 | 1/2005 |
| WO | WO 2005/004970 A1 | 1/2005 |
| WO | WO 2005/014055 A2 | 2/2005 |
| WO | WO 2006/005349 A2 | 1/2006 |
| WO | WO 2006/017439 A2 | 2/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/121183 A1 | 11/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/039910 A2 | 4/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010975 A1 | 1/2009 |
| WO | WO 2009/017541 A1 | 2/2009 |
| WO | WO 2009/139878 A1 | 11/2009 |
| WO | WO 2010/006620 A1 | 1/2010 |
| WO | WO 2010/130261 A1 | 11/2010 |
| WO | WO 2011/011023 | 1/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011/079129 A1 | 6/2011 |
| WO | WO 2011/109393 A1 | 9/2011 |
| WO | WO 2011/147803 A1 | 12/2011 |
| WO | WO 2012/006629 A2 | 1/2012 |
| WO | WO 2012/013662 A1 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/079590 A1 | 6/2012 |
| WO | WO 2012/085107 A2 | 6/2012 |
| WO | WO 2012/110755 A2 | 8/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012/166045 A1 | 12/2012 |
| WO | WO 2012/166967 A1 | 12/2012 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013/083137 A1 | 6/2013 |
| WO | WO 2013/098190 A1 | 7/2013 |
| WO | WO 2013/105091 A1 | 7/2013 |
| WO | WO 2014/062225 A1 | 4/2014 |
| WO | WO 2014/063711 A1 | 5/2014 |
| WO | WO 2014/074142 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/176867 A1 | 11/2014 |
| WO | WO 2015/184365 | 12/2015 |

OTHER PUBLICATIONS

International Search Report dated Feb. 24, 2015, for International Application No. PCT/US2014/053573.
International Search Report and Written Opinion for International Application No. PCT/US2015/033344 dated Mar. 12, 2015.

(56) References Cited

OTHER PUBLICATIONS

Total Body Relief and Hygiene for Travel, Home bath, and life's less comfortable moments, http://www.biorelief.com/blog/self-cath-fits-in-your-pocket/ dated Apr. 19, 2014.

* cited by examiner

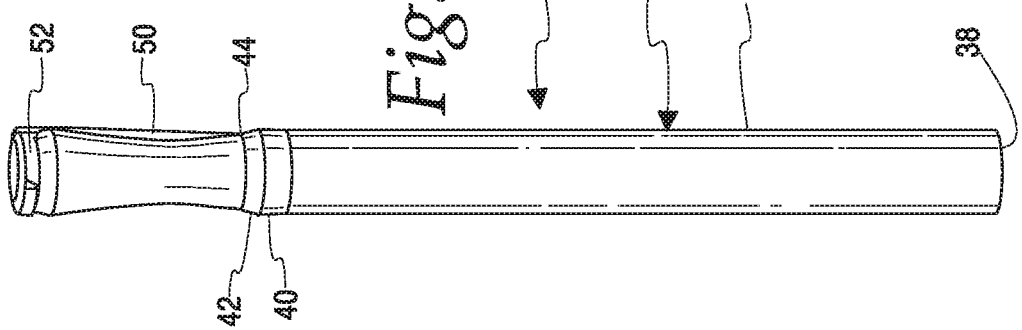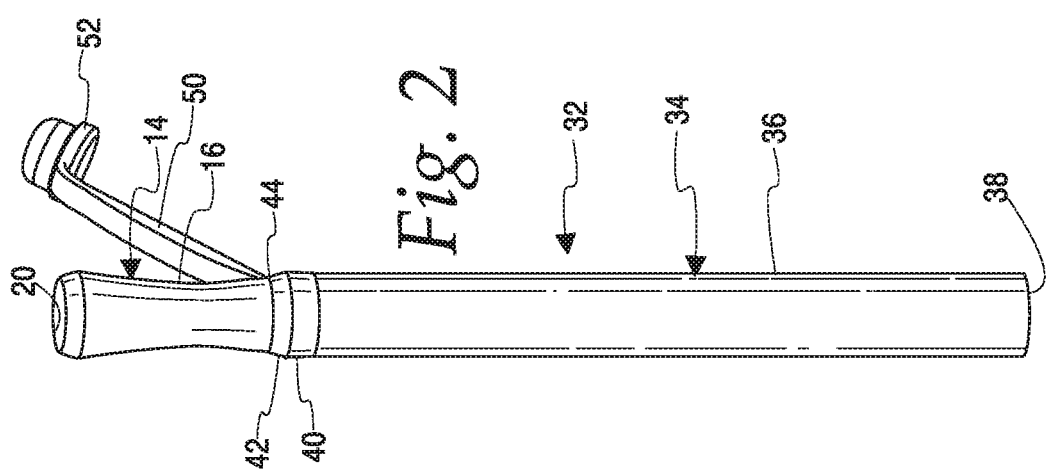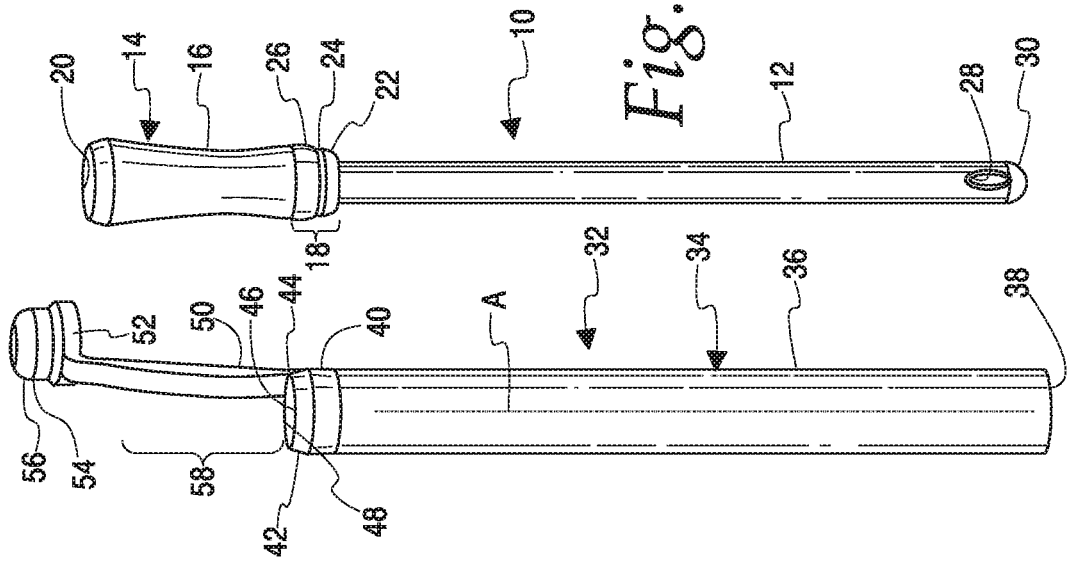

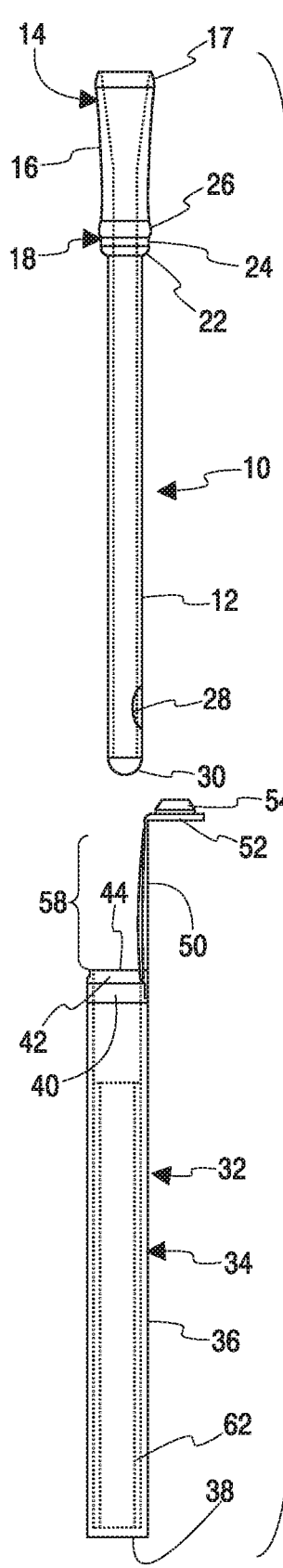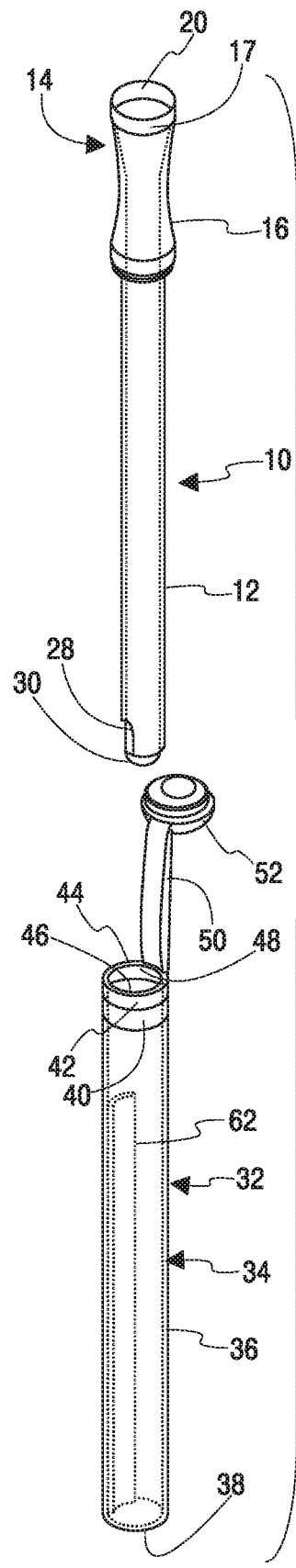

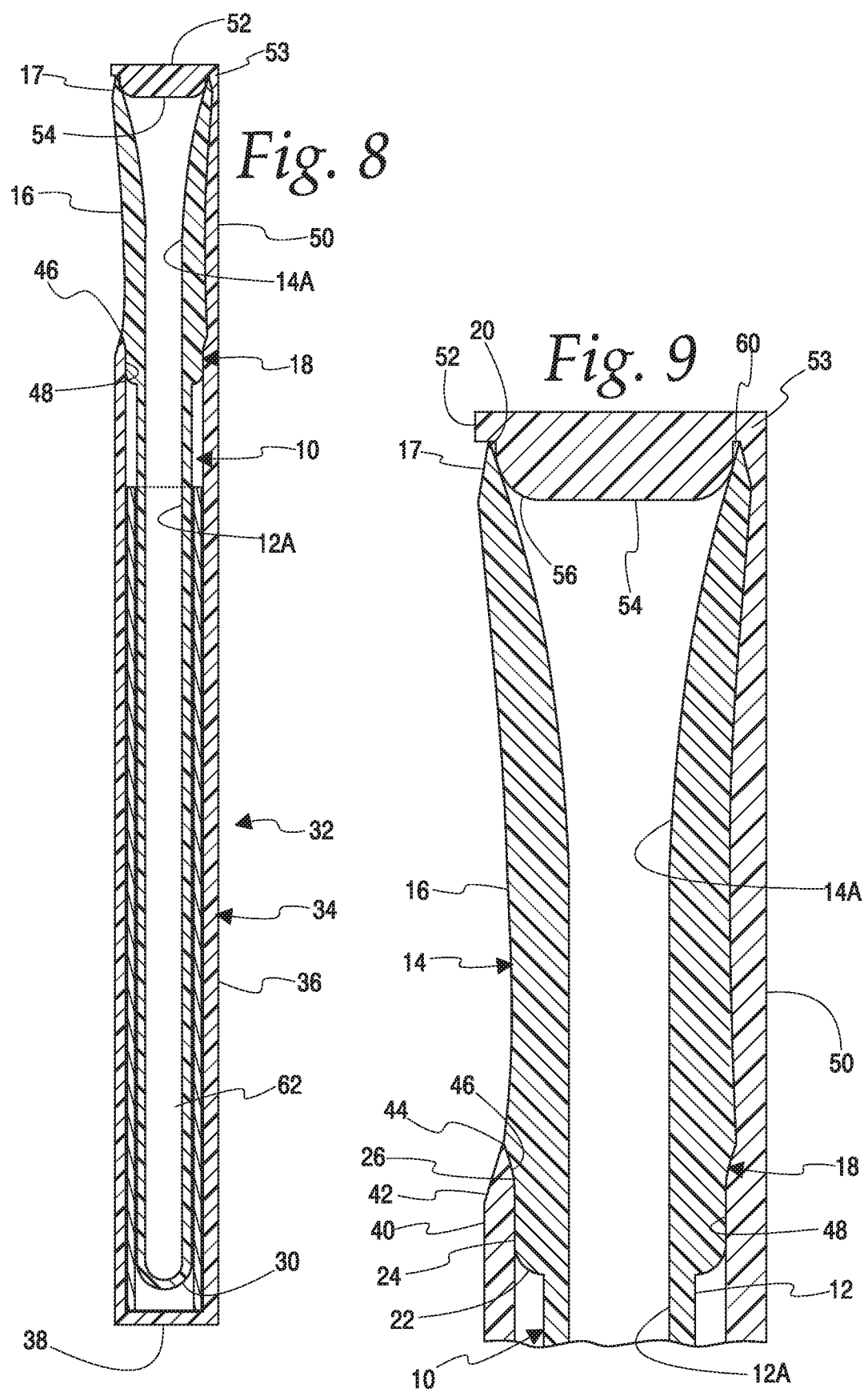

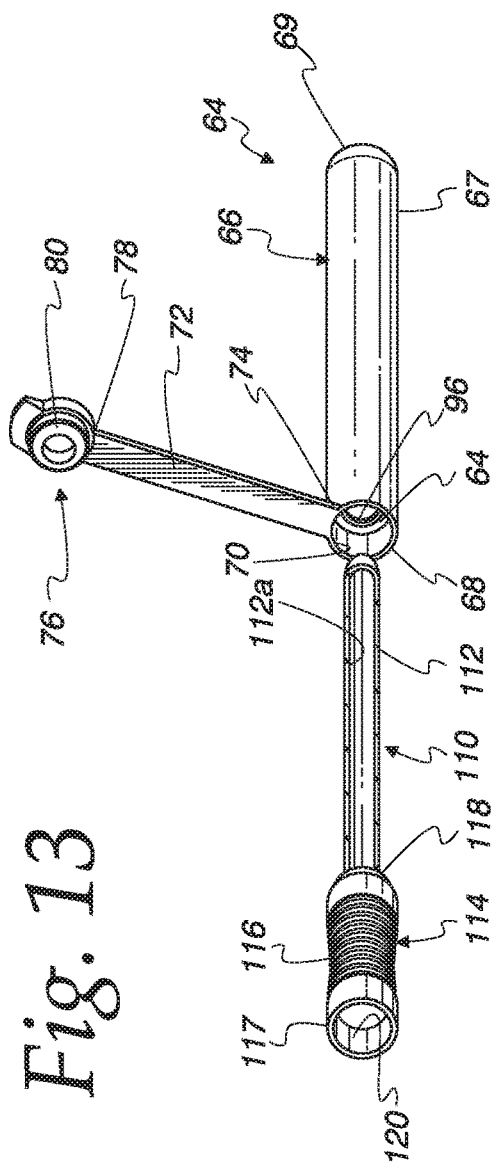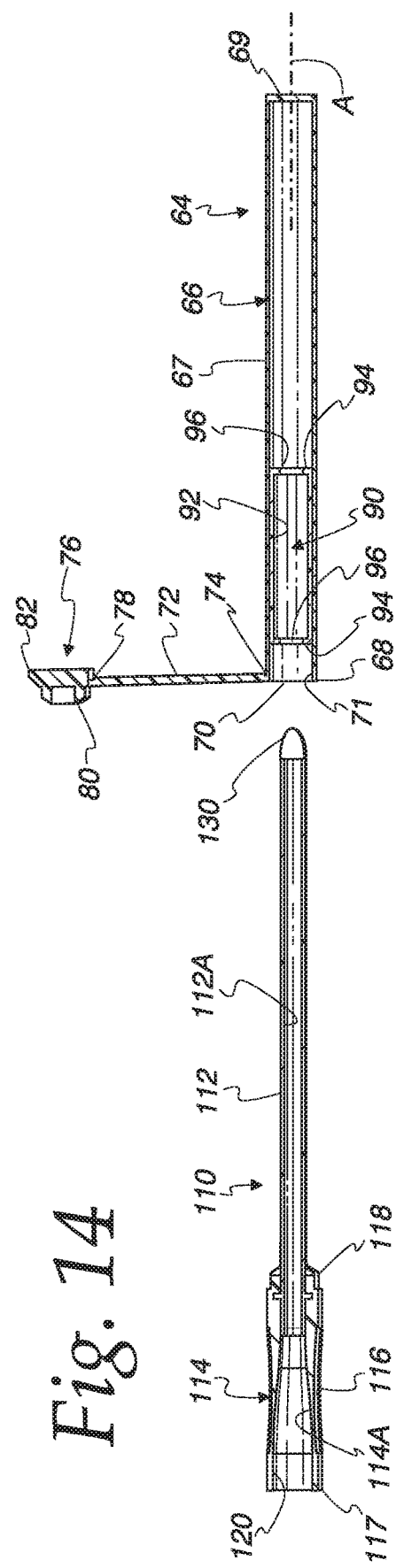

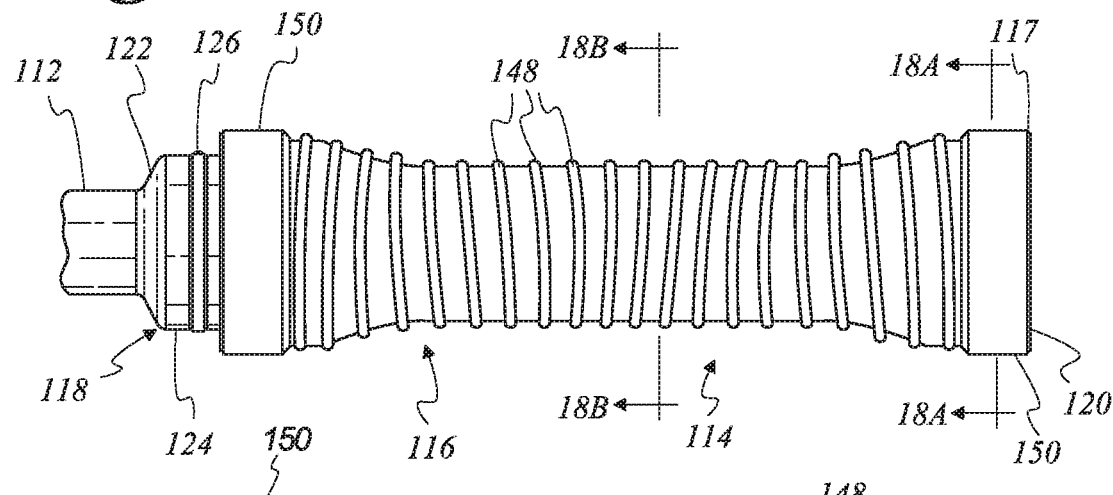
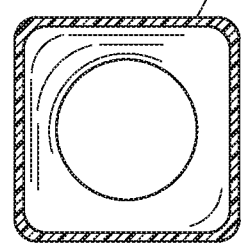
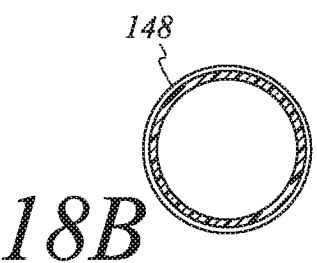
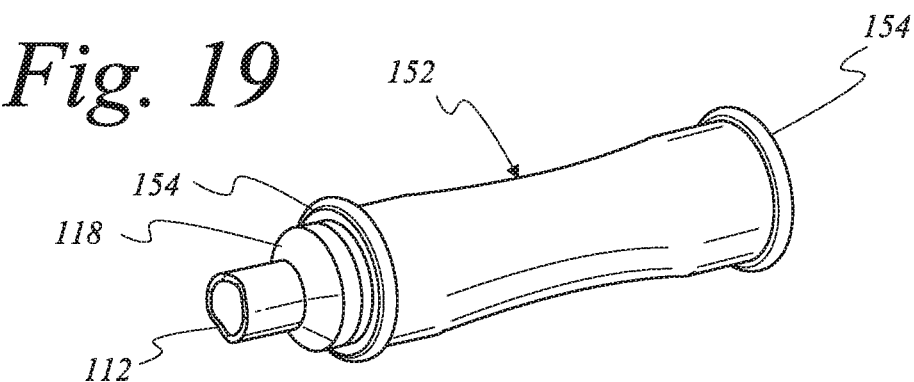
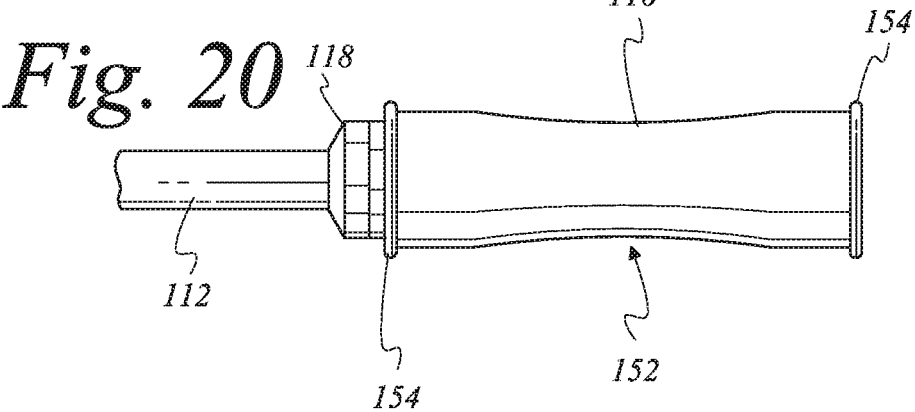

Fig. 23
Fig. 24
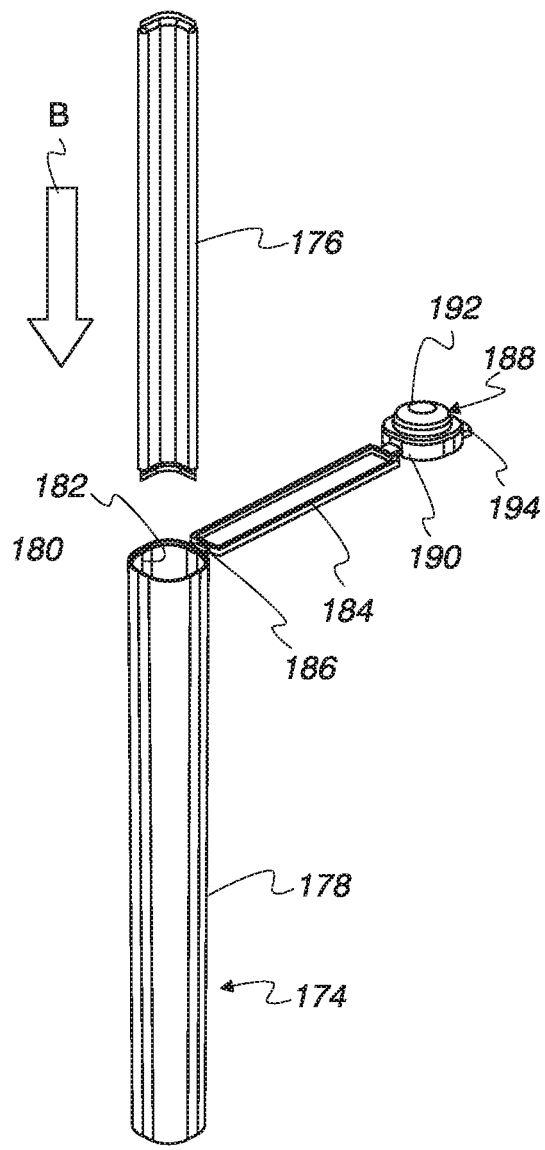
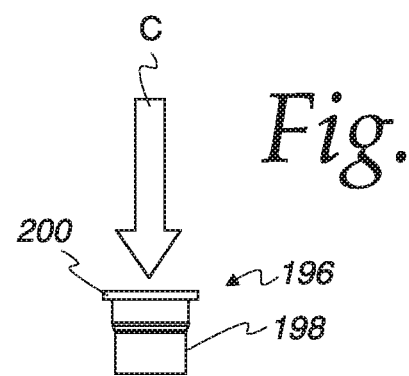
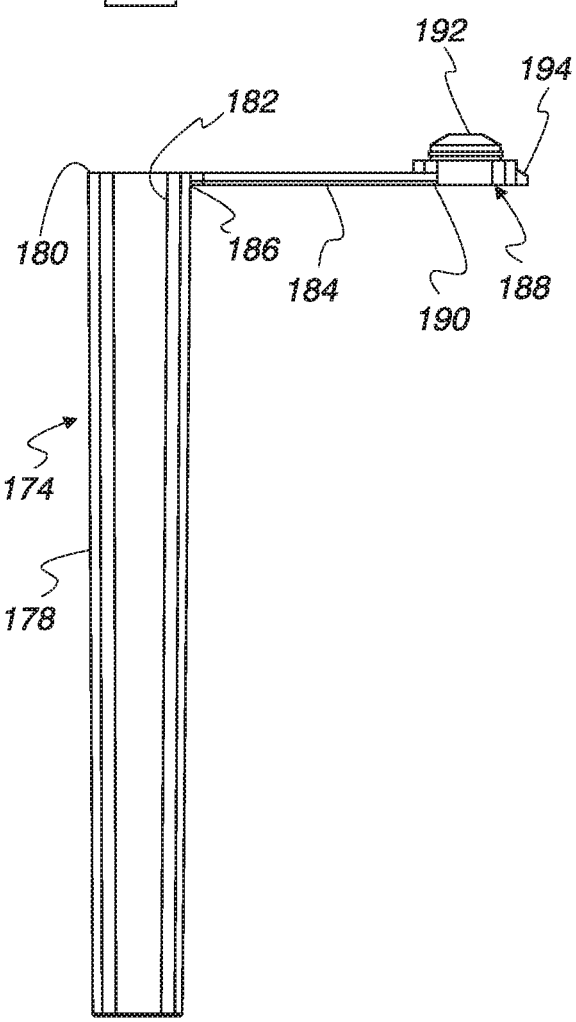

FLIP OPEN CATHETER PACKAGE

RELATED APPLICATION

This application is a Divisional of U.S. application Ser. No. 15/314,436, filed Nov. 28, 2016 which is a U.S. National Stage of PCT of International Patent Application No. PCT/US2015/033344, filed May 29, 2015 which claims the benefit of and priority to U.S. Provisional Patent Application Ser. No. 62/005,635, filed May 30, 2014, the contents of which are incorporated by reference herein.

FIELD OF THE DISCLOSURE

This disclosure relates generally to packaging for medical devices such as urinary catheters. More particularly, this disclosure relates to compact catheters, such as urinary catheters, and the packaging, storing and hydrating/lubricating of such catheters.

BACKGROUND

Intermittent catheterization is a good option for many users who suffer from various abnormalities of the urinary system. A common situation is where single use, individually packaged, sterile catheters are used. Catheters often include a surface treatment that reduces friction to allow for easier and less traumatic insertion into and through the user's urethra.

One such surface treatment includes providing a hydrophilic coating on the exterior surface of the catheter. In a hydrophilic coated catheter, the catheter is provided with a thin coating disposed on the outer surface of the catheter. When this coating is activated by contact with a hydrating medium, such as liquid water or water vapor, it becomes lubricious and provides an extremely low coefficient of friction surface.

The hydrating medium may be added to the catheter package after opening. Another embodiment provides liquid water in a separate compartment that is opened to allow the water to enter the catheter containing compartment for direct contact with the hydrophilic coating. Or the hydrating medium could be a wick, sachet or liquid sequestering element wetted with a liquid, such as water. Water vapor from the wick hydrates the catheter. Catheter packages employing a wick are described in greater detail in U.S. Pat. Nos. 8,205,745 and 8,356,457 to Murray et al. and in U.S. Patent Application Publication Nos. 2009/0131917 to Kavanagh et al. and 2012/0228165 to Murray et al., all of which are incorporated herein by reference.

Another type of surface treatment is a gel-coated catheter in which a gel-lubricant is applied to the surface of the catheter. The gel-lubricant may be applied to the catheter surface just before or during the packaging operation or as the catheter is being inserted by the user.

Regardless of whether a surface treatment is used or what type of surface treatment is used, some type of package for the catheter is required. In the past various kinds of packages have been used, including molded containers of assorted sizes and shapes, bags and pouches made of plastic or metal foil, and similar kinds of devices. An example of a tubular type of package is shown in U.S. Published Application No. 2005/0043715. While these prior art packages generally accomplish the objective of protecting the catheter during transport, storage and preparation for use, they suffer from disadvantages that range from fundamental—the packages break open prematurely; to economic—the package designs are wasteful of material and labor; to the annoying—the packages confuse users as to how to open them, or the packages tend to spill the hydrating medium upon opening. What is needed is a catheter package that is economical to manufacture and fill, reliable throughout its useful life, and simple and intuitive to use. It is also desirable to have a compact package whose transport and use can be discreet.

SUMMARY

In one aspect, the catheter package of the present disclosure includes an elongated case having a closed end and a rim at the opposite end. The rim defines an open end of the case. The package further includes a cap which is tethered to the case by a flexible strap. The case is sized to receive and enclose the tubing portion of a catheter. The funnel of the catheter is releasably engageable with the package case at or near the rim, with all or most of the funnel remaining on the exterior of the case. The engagement of the funnel with the case near the rim seals any hydrating medium in the case. The cap is releasably engageable with the funnel. The strap length is such that when the cap is engaged with the funnel the strap and cap will retain the funnel in contact with the case at the open end. Preferably the cap snaps into and closes the open end of the funnel to prevent entry of contaminants into the funnel and to prevent any hydrating medium from exiting the package through the tubing and funnel. A user can flip the cap off the funnel and flex the strap slightly away from the axis of the case to permit removal of the catheter from the case. After use the catheter can be replaced in the case and the cap can be reclosed if a user so chooses. The strap may be integrally molded In another aspect, the present disclosure concerns a package of the type described having a grommet in the interior of the case. The grommet is filled with a lubricating gel. Upon removal of the catheter from the package the catheter tubing is drawn through the lubricating gel in the grommet, thereby coating the catheter tubing with gel and making it ready for use.

In still another aspect, the present disclosure is directed to a catheter specially adapted for use with the package of the type described. Since the package does not have a hygienic sleeve for the catheter, the user is dependent on the funnel for catheterization as they cannot touch the catheter tube (due to possible contamination issues). To improve the user's grip on the funnel during general use of the catheter it is beneficial to provide ridges on the funnel. Alternately, the funnel's overall shape could also improve grip. From a touch perspective a tactile zone on the funnel ends allows the user to feel when they are near an end of the funnel. This decreases the probability of the user's fingers accidentally slipping from the funnel and contacting the catheter tubing or urine.

The package of the present disclosure can also be adapted for use with a male catheter. Male catheters are difficult to fit inside a compact package. The male catheter of the present disclosure addresses this by being folded inside the case of the package. The outer grip portion of the catheter may be made slideable along the catheter to be used as a gripper and enhance hygienic benefits.

In packages having a hydrating sachet it may be advantageous to add an adaptor to the top of the package case. The adaptor is press fit into the opening at the top of the case. The adaptor has an external cross section that matches the internal cross section of the package case. It also has an internal passageway whose cross section matches that of a seal section on either the bottom of the funnel or the end of the catheter.

An alternate form of hydration can be the straightforward addition of liquid water to the package case prior to installation of the catheter. Following introduction of about 1.5 ml of water to the case, a molded liner is inserted into the case. The liner has a flange on one end that is press fit into the opening at the top of the case to form a seal between the liner and the case. Then the catheter is inserted into the liner. The bottom of the funnel has a portion which may fit inside the liner in a press fit seal. Then the strap of the case is folded up and the cap on the end of the strap is folded down onto the top end of the funnel. Finally, a tamper-evident label may be placed on the closed cap to complete the package. A further alternate form uses the liner as just described but replaces the strap-retained cap with a fully removable hollow cap that encloses the catheter funnel and is removably connectable to the case. A further alternate form of hydration could be the addition of liquid water in the package case but without the liner just described. In this embodiment the liquid water would be in the package case alongside the catheter.

In another aspect a flexible label could be substituted for the molded strap. The label may be adhesively secured to the case and extend to a point of attachment with the cap. Attachment of the label to the cap may be either adhesive or mechanical or both.

BRIEF DESCRIPTION OF THE DRAWINGS

FIG. 1 is a perspective view of a catheter package according to the present disclosure with a catheter of the type suitable for use with the package shown adjacent to the package.

FIG. 2 is a perspective view of a catheter package assembly having the catheter installed in the package but with the cap of the package in an uninstalled position.

FIG. 3 is a perspective view of the catheter package assembly with the catheter and cap both in their installed positions.

FIG. 6 is a side elevation view of the catheter package of FIG. 1 with the catheter removed and shown above the package and with a hydrating wick shown in hidden lines in the case.

FIG. 7 is a perspective view similar to FIG. 6.

FIG. 8 is a longitudinal section of the package and catheter in the assembled condition.

FIG. 9 is a longitudinal section of the open end of the case with a funnel engaged by the cap, on an enlarged scale.

FIG. 13 is a perspective view of a catheter package according to the present disclosure with a gel grommet therein and a catheter, partially in section, of the type suitable for use with the package shown adjacent to the package case.

FIG. 14 is a longitudinal section through the catheter package assembly of FIG. 13 with the catheter aligned for installation in the package case.

FIG. 18 is a side elevation view, further enlarged, of the funnel of the catheter of FIGS. 16 and 17 illustrating the texture of the funnel surface.

FIG. 18A is a section taken along line 18A-18A of FIG. 18.

FIG. 18B is a section taken along line 18B-18B of FIG. 18.

FIG. 19 is a perspective view of a further alternate form of a funnel.

FIG. 20 is a side elevation view of the funnel of FIG. 19.

FIG. 23 is a perspective view of a first step in an assembly process for a package hydrated by a sachet.

FIG. 24 is a side elevation view of a second step in an assembly process for a package hydrated by a sachet, illustrating installation of an adaptor.

DETAILED DESCRIPTION OF THE EMBODIMENTS

Figure 4:
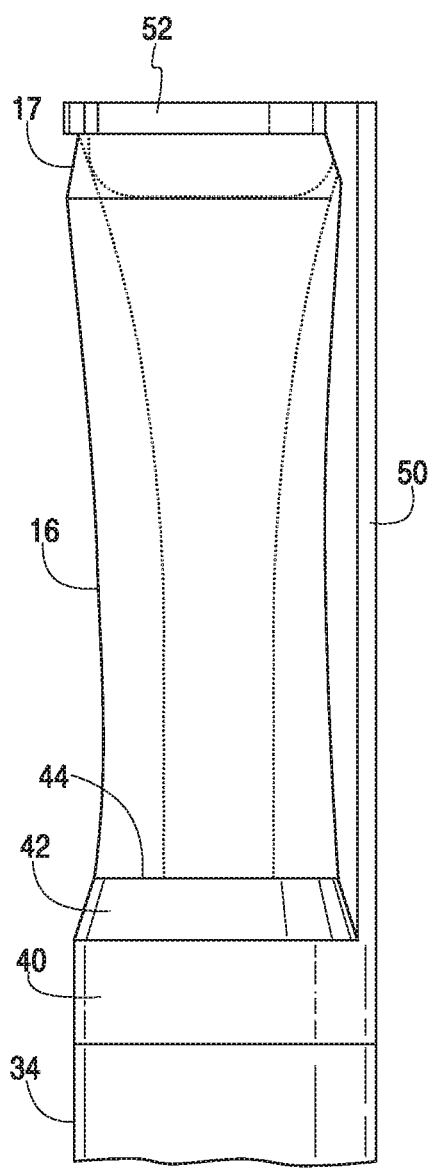
FIG. 4 is a side elevation view of the open end of the case with a funnel engaged by the cap, on an enlarged scale.

The present disclosure is directed to a catheter package for an intermittent catheter. The catheter itself is shown at 10 in FIG. 1. It has an elongated, hollow tubing 12 attached at one end to a hollow funnel 14. The funnel is sometimes alternately referred to as a connector or a grip. The tubing and funnel each define a central lumen therein. The tubing lumen 12A and the funnel lumen 14A can be seen in FIGS. 8 and 9. The lumens of the tubing and funnel fluidly communicate with one another as is conventional. The catheter 10 can be an injection molded component with the grip/funnel 14 being integral with the tubing 12. Other manufacturing methods for the catheter are possible.

The funnel 14 has an upper body portion 16 and a lower seal portion shown generally at 18. The upper or free end 17 (FIG. 4) of the body portion 16 defines a funnel opening 20. While the body portion 16 is shown having a gently curved outer surface that is somewhat hyperbolic in nature, it will be understood that other exterior shapes for the funnel are possible, such as a frusto-conical shape, perhaps with a suitable lip on the free end. Whatever the exterior shape, the funnel 14 generally has an outer diameter greater than that of the catheter's tubing 12. This size, plus the fact that the funnel is not lubricated, makes the funnel 14 a convenient location for grasping the catheter 10 to manipulate it. The funnel may be suitable for connection to a drainage bag, other tubing or any other appropriate apparatus as is conventional. For example, the opening 20 defined in the free end 17 of the funnel may be large enough to receive a urine bag connector.

Further details of the seal 18 at the lower end of the funnel include a beveled lower portion 22 joining a cylindrical transition section 24 which is adjacent to a bead 26. The bead 26 may have a somewhat larger outside diameter than the transition section 24 for reasons that will become evident below. The beveled lower portion 22 assists in guiding the seal portion 18 into the package as explained below. Other embodiments for the seal portion are possible as each of the components described above may not be necessary in all instances.

At least one radial eyelet 28 is formed in the tubing 12 at the end of the tubing farthest from the funnel 14. The eyelet provides fluid access to the central lumen 12A of the tubing 12. Adjacent the eyelet 28 is a rounded tip 30 that provides a smooth surface to facilitate insertion of the tubing into a urethra. In some embodiments it may be desirable to include more than one eyelet.

Turning now to the catheter package, it is shown generally at 32 in FIG. 1. The package may include an elongated, hollow case 34 which has an axis A defined by a generally tubular wall 36. The wall may have cylindrical inside and outside diameters. Or the inside dimension of the wall 36 may be cylindrical while the outside dimension may be non-cylindrical, e.g., a shape with flat sides joined by arcuate corners. Alternately, the entire case 34 could have a non-circular cross-section. The tubular wall 36 joins a bottom or end wall 38 that closes the bottom of the case 34. At the other end of the case there may be an annular band 40 that merges with an externally tapered section 42 of the wall 36. Tapered section 42 terminates at a rim 44. The rim 44 defines an opening 46 at the top of the tubular wall 36. From the rim 44 and extending axially for at least the distance opposite the tapered section 42, and preferably somewhat axially beyond the tapered section, the internal surface of the tubular wall 36 defines an internal seal face 48. Thus, in one embodiment, when the catheter 10 is installed in the package 32, the internal seal face 48 may engage the bead 26 and transition section 24 of the funnel seal 18 in an interference fit which provides a seal between the funnel and package.

Figure 5:
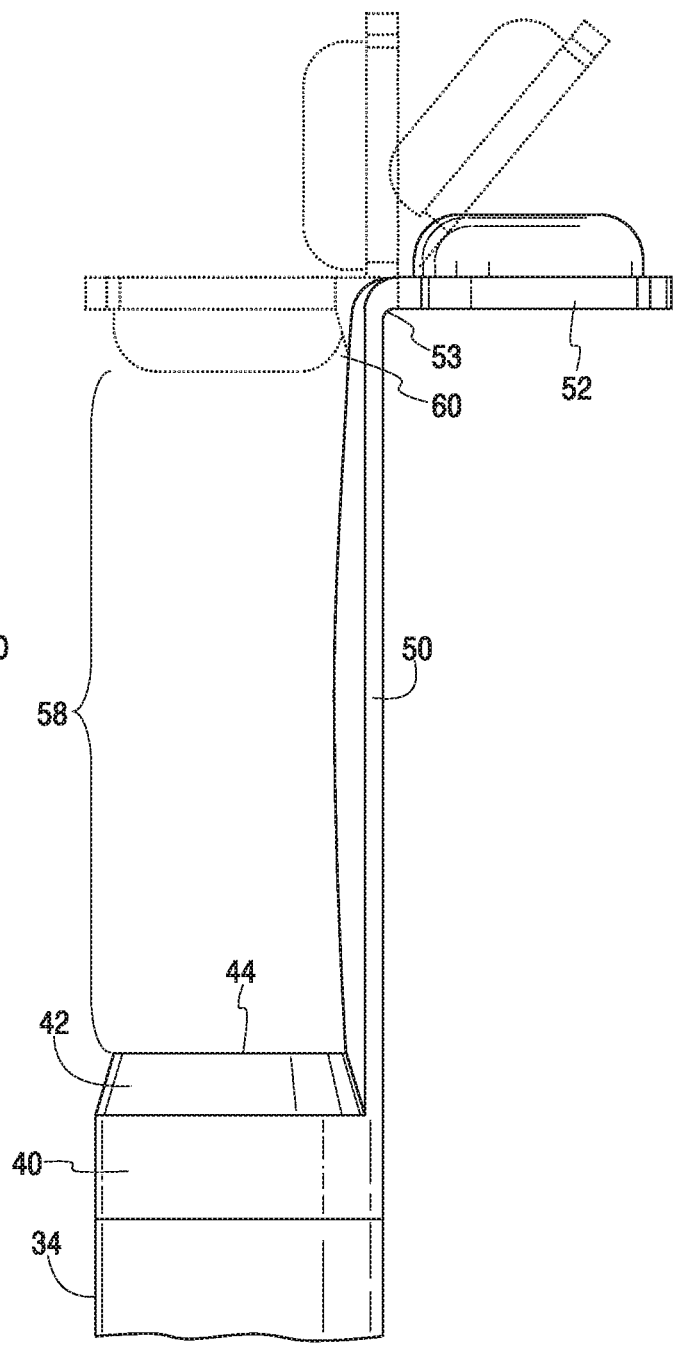
FIG. 5 is a view similar to FIG. 4 but with the catheter removed.

In one embodiment, the package further may include a strap 50. The strap 50 is an elongated, flexible member which is fixedly attached to the tubular wall 36, preferably at the annular band 40 and tapered section 42 of the tubular wall 36 as best seen in FIGS. 4 and 5. The other end of the strap 50 mounts a cap 52. The cap is joined to the strap by, for example, a living hinge 53. It will be understood that while a living hinge is a convenient method of connecting the cap and strap, other types of hinges are possible. The underside of the cap 52 carries a boss 54. The boss may have a rounded edge 56. In the present embodiment the strap 50 extends axially beyond the rim 44 such that the cap 52, strap 50 and rim 44 define a pocket 58 or space for receiving the funnel 14. The pocket 58 is sized to accommodate the funnel 14 between the cap 52 and the rim 44. Thus, the cap 52 does not engage the case 34, rather it is releasably engageable with the body portion 16 of the funnel 14.

The boss 54 is spaced laterally from the strap 50 so that there is a space 60 for the free end 17 of the funnel to fit between the boss 54 and the strap 50, as best seen in FIG. 9. When the cap is closed on the funnel, the rounded edge 56 of the boss 54 leads into the opening 20 in the free end of the funnel 14, producing contact between the boss and the internal wall of the funnel. This creates an interference fit and a seal between the boss and the internal surface of the funnel.

Cooperation between the catheter 10 and package 32 is illustrated in FIGS. 2 and 3. To install the catheter in the package the strap 50 may optionally be moved away from the case opening 46 by flexing the strap 50 generally in a radial direction. The catheter tubing 12 enters the case 34 through the opening 46. The inside diameter of the tubular wall 36 is greater than the outside diameter of the tubing 12 so the tubing fits in readily. However, the inside diameter of the opening 46 is slightly less than the outside diameter of the funnel body portion 16. Thus, while the seal 18 of the funnel 14 will enter the case 34 in an interference fit, the remainder of the funnel will not enter the case. Accordingly the body portion 16 of the funnel remains external to the case 34 and in the space which defines the pocket 58.

Once the catheter tubing 12 is inside the case 34 and the funnel seal portion 18 is snug against the seal face 48, the strap 50 may, if need be, be flexed somewhat to return the strap to a position where it is adjacent the funnel body 16 and generally parallel to the case axis A. Then the cap 52 is rotated essentially 180° about the hinge 53 as shown by the phantom line positions of the cap in FIG. 5. This will allow the boss 54 to fit in the funnel opening 20 as seen in FIG. 3. The cap 52 and strap 50, together with the interference fit between the seal 18 and case 34, retain the catheter 10 in the package 32. The strap has sufficient tensile strength to prevent elongation that might otherwise permit the catheter to come out of the case.

FIGS. 6 and 7 illustrate a possible embodiment of a hydrating medium. This could take the form of a wick 62 or a sachet. The wick is placed in the case 34 either prior to or simultaneous with the installation of the catheter. The wick in this embodiment is basically a rectangle initially. It will become curved once it is placed in the cylindrical case 34. Water vapor emanating from the wick 62 will lubricate the coating on the tubing. The seal 18 on the inner end of the funnel 14 will close the case opening 46 and the cap 52 will close the funnel opening 20 to prevent dissipation of the moisture from the interior of the case 34.

FIGS. 8 and 9 further illustrate the two seals just described. Here it can be seen that with the catheter 10 installed in the package 32, there is an interference fit between the internal seal face 48 of the case 34 and the bead 26 and transition section 24 of the funnel seal 18. That is, at least the bead 26, and preferably the bead 26 and transition section 24, are compressed as they enter the top of the case 34. The resulting interference fit provides a seal between the funnel 14 and package 32. This seals the space inside the case 34. The funnel lumen 14A is sealed by the cap 52 and its boss 54. The boss fits down inside the opening 20 of the funnel in an interference fit while the underside of the cap engages the outer edges of the funnel to complete the seal of the funnel lumen 14A.

When the time comes for the catheter to be put to use, a user can simply flip open the cap 52, removing the boss 54 and cap 52 from engagement with the funnel 14. The strap 50 can be pressed aside slightly to permit the user to grasp the funnel and pull the catheter out of the package. If a surface coating was applied to the catheter tubing and a hydrating medium was placed in the package, then the catheter is immediately ready to use. If not, a hydrating medium could be added to the package to lubricate the catheter. Or a gel-coating could be applied to the tubing 12.

It will be noted that the flip open cap 52 is intuitive and familiar to open as it has a similar feature to standard package openings, e.g. a plastic ketchup bottle lid. The product signifies the correct orientation for opening such that there will not be spillage upon opening the product. There can be a tamper-evident label joining the cap to the funnel. The package 32 can be molded as one piece and the catheter can also be a molded component thereby minimizing the cost. The product size can be minimized by keeping to a minimum diameter required for connection to a drainage bag. Another advantage is the package is reclosable and allows for carrying the product after use for later disposal without any leakage or odors.

Figure 10:
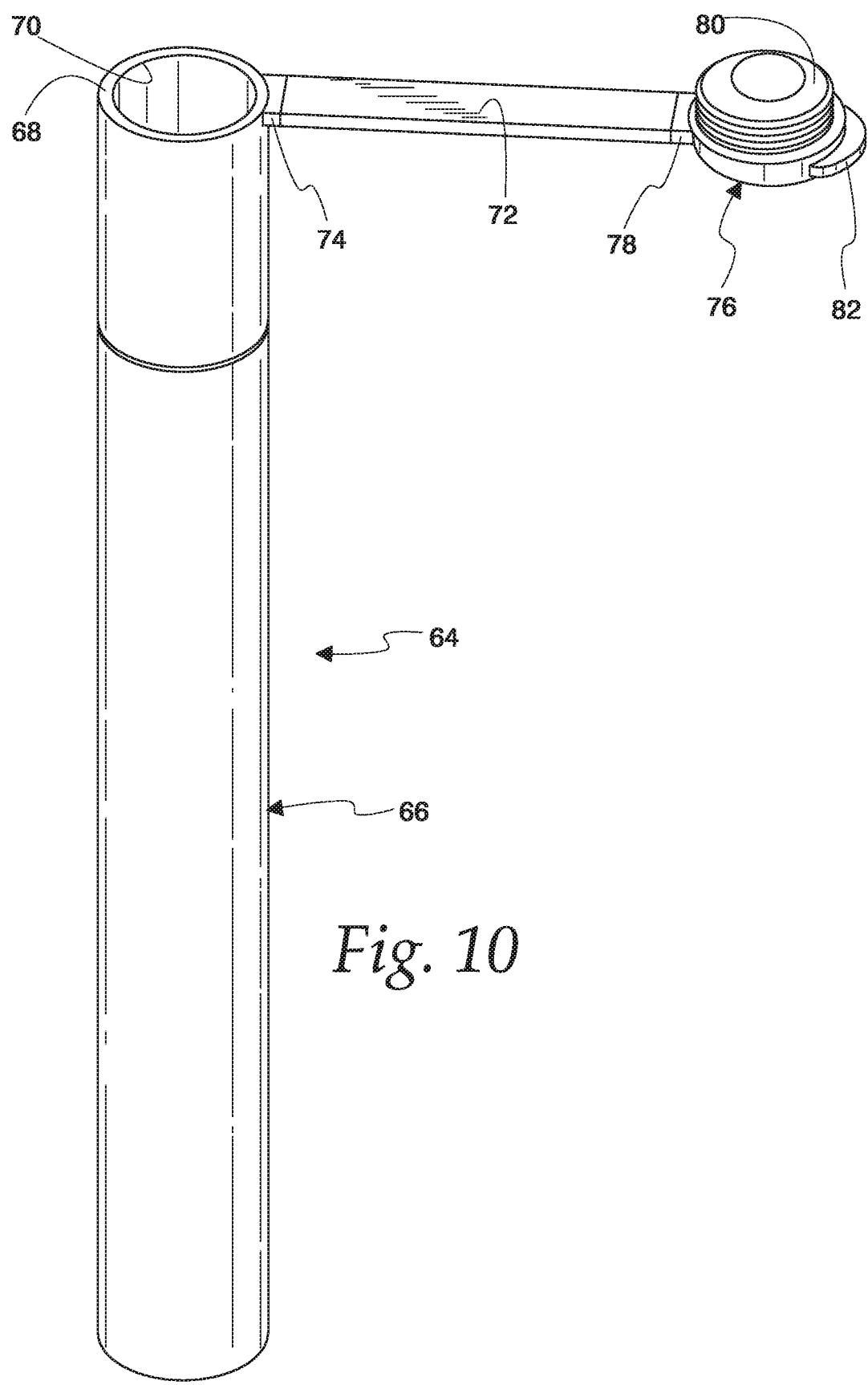
FIG. 10 is a perspective view of an alternate embodiment of the package.
Figure 11:
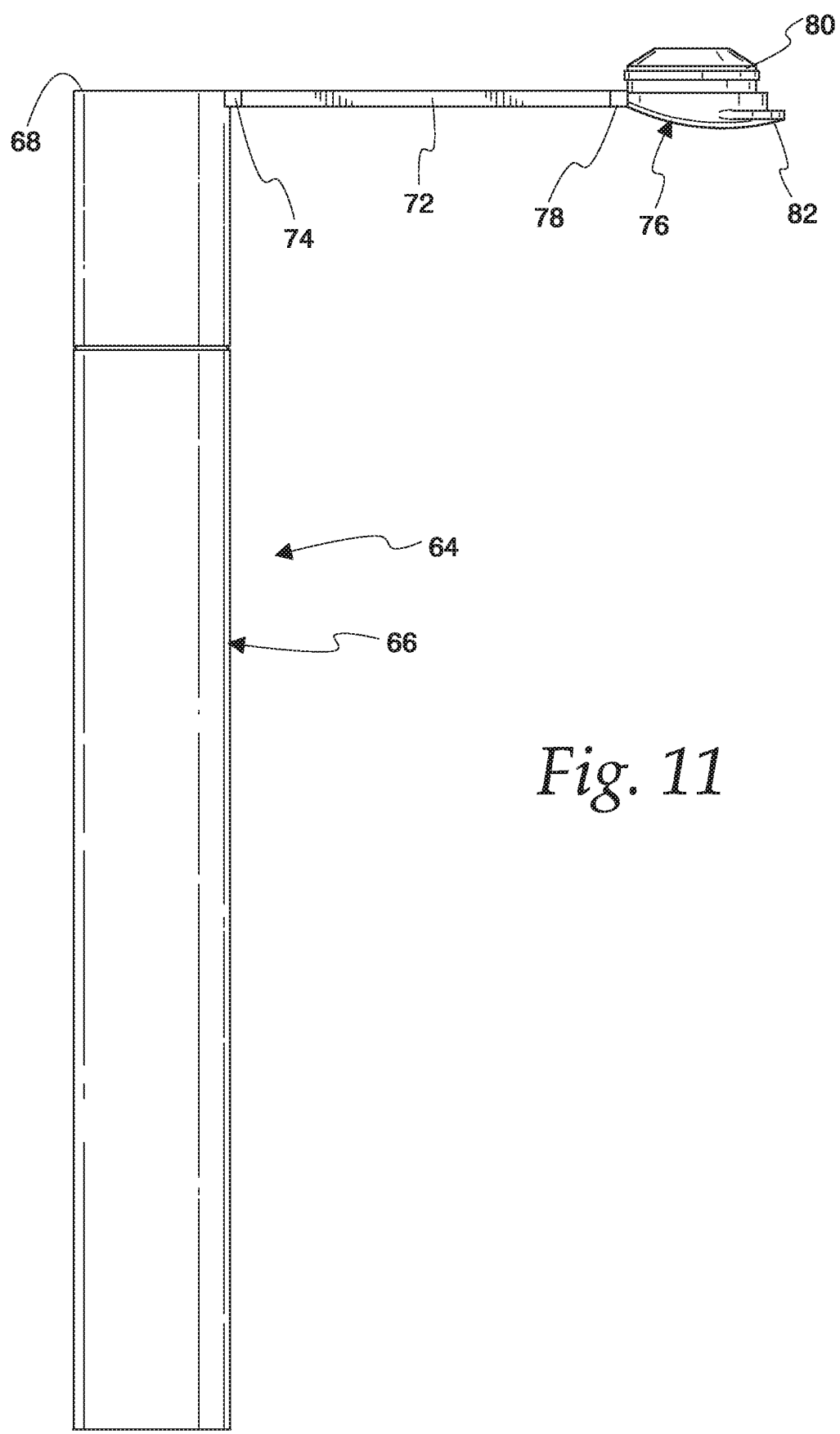
FIG. 11 is a side elevation view of the package of FIG. 10.

FIGS. 10 and 11 illustrate an alternate embodiment of the package generally at 64. This embodiment has a case 66 which is similar to the case 34. The case 66 terminates at a rim 68 which defines an opening 70. As in the previous embodiment the case 66 is sized to receive a catheter tubing and the seal portion of a funnel body. The body portion of the funnel will remain on the exterior of the case. The package 64 has a strap 72 which is attached at one end to the case 66 at a hinge 74. A cap 76 is attached to the other end of the strap 72 by a second hinge 78. Hinges 74 and 78 are preferably living hinges although it could be otherwise. The cap 76 is similar to cap 52 and thus it includes a boss 80. The cap 76 may further include a tab 82 extending from an edge of the cap to assist a user in removing the cap from a catheter funnel.

As can be seen in FIGS. 10 and 11 the strap 72 initially extends radially of the case 66, rather than axially as in the previous embodiment. In a common orientation of the package as shown in the drawings, this will place the strap in a horizontal plane. Accordingly, once a catheter has been installed in the case, the strap will be folded up approximately 90° about the hinge 74, thereby placing the strap adjacent the funnel. At this point the cap 76 will be folded down approximately 90° about the hinge 78, placing the cap over the free end of the funnel body, with the boss 80 inside the opening 20 of the funnel.

Figure 12:
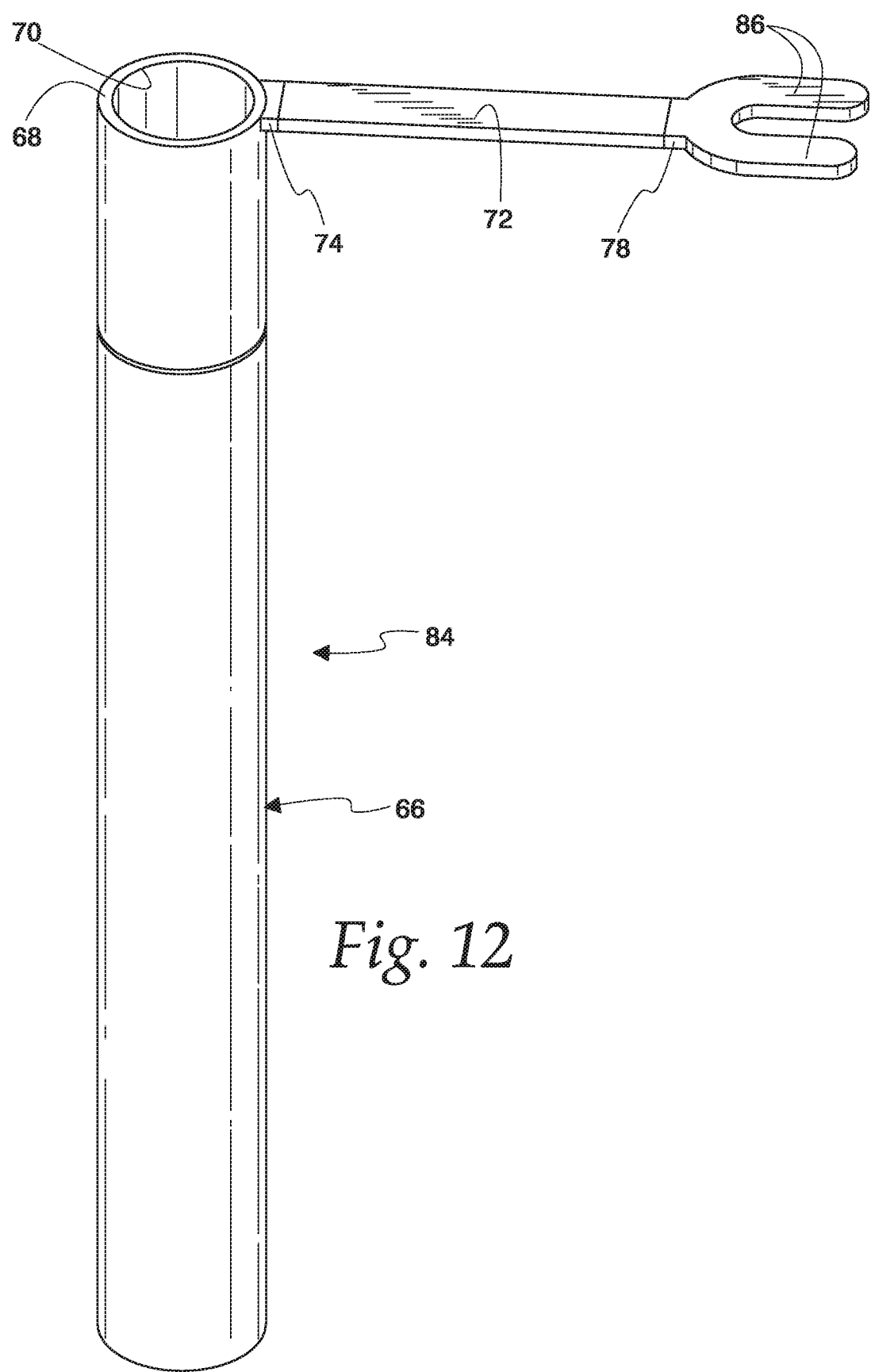
FIG. 12 is a perspective view of a further alternate embodiment of the package.

It is pointed out that while the cap is shown as a part that snaps into the free end of the funnel, it could be otherwise. FIG. 12 illustrates such an alternate embodiment generally at 84 wherein a variation of the cap is shown. Package 84 has a cap in the form of a fork having a pair of spaced apart fingers 86. The fingers are sized and spaced so as to be engageable with the side wall of the funnel at its point of smallest diameter. The pair of fingers 86 engage the funnel between them. In this case an additional cover for the funnel opening may be needed.

It should be understood that various changes and modifications to the presently preferred embodiments described herein will be apparent to those skilled in the art. Such changes and modifications can be made without departing from the spirit and scope of the invention disclosed herein. For example, while the funnel is shown engaging the internal surface of the case, the arrangement could be reversed. That is, the funnel could have an external flange or the like that engages the external surface of the case, leaving the internal surface of the case spaced from an interior portion of the funnel.

Also, while it is considered advantageous to manufacture the case, strap and cap as one integral part, alternatively these components could be formed initially as one or more separate parts which are subsequently fastened together. Thus, the strap could be manufactured as a part separate from the case and then subsequently fastened to the case using a suitable connection method. Similarly, the cap could initially be formed separate from the strap and then connected to the strap. In a similar vein, the case could be made of separate parts, such as a separate bottom wall that is fixed to the tubular wall.

While the strap has been shown having initial (that is, prior to closure on a funnel) orientations that are either axial or radial to the case axis, it will be understood that other initial orientations are possible so long as the strap can be moved to a point where the cap can releasably engage the exposed portion of the catheter. Also, the initial angle of the cap relative to the strap could also be other than as shown. Thus, the cap could have an initial position similar to one of the phantom showings of FIG. 5. Also, the strap and cap need not necessarily fold abruptly about the hinge lines shown. The strap could form a loop that gradually transitions from the case to a point where the cap attaches to the funnel.

Further alternate structures could include a cap having a gripping member that is adhesively attached to the outer wall of the funnel. That is, the end of the strap could carry an adhesive gripping member arranged to releasably engage the side and/or the top of the funnel. In another arrangement both the strap and cap could comprise an integral adhesive gripping member. In this case the strap and cap would be a piece of flexible tape adhered at one portion of the tape to the exterior surface of the case's tubular wall and at another portion of the tape to the funnel. The tape would have a length enabling it to extend from the tubular wall to the funnel. It would be advantageous to have the tape extend over the free end of the funnel to close off and seal the funnel opening. Or the tape could extend from one side of the tubular wall, up and over the free end or top of the funnel and then back down to the other side of the tubular wall. The user would remove the tape from the funnel to enable pulling the catheter out of the package for use.

Figure 15:
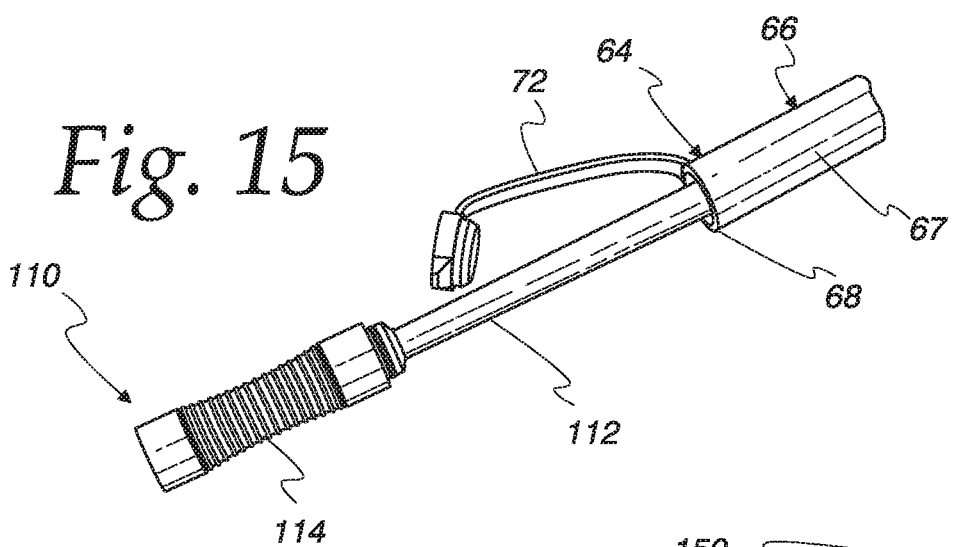
FIG. 15 is a somewhat enlarged perspective view of the catheter package assembly of FIG. 13 with the catheter being partially removed from the package case.

An alternate method of catheter hydration is shown in the catheter package assembly shown in FIGS. 13-15. The catheter itself is shown at 110. It has an elongated, hollow tubing 112 attached at one end to a hollow funnel 114. The funnel is sometimes alternately referred to as a connector or a grip. The tubing and funnel each define a central lumen therein. The tubing lumen 112A and the funnel lumen 114A can be seen in FIGS. 13 and 14. The lumens of the tubing and funnel fluidly communicate with one another as is conventional. The catheter 110 can be an injection molded component with the grip/funnel 114 being integral with the tubing 112. Other manufacturing methods for the catheter are possible.

The funnel 114 has an upper body portion 116 and a lower seal portion shown generally at 118. The upper or free end 117 of the body portion 116 defines a funnel opening 120. While the body portion 116 is shown having a gently curved outer surface that is somewhat parabolic in nature, it will be understood that other exterior shapes for the funnel are possible, such as a frusto-conical shape, perhaps with a suitable lip on the free end. Whatever the exterior shape, the funnel 114 generally has an outer diameter greater than that of the tubing 112. This size, plus the fact that the funnel is not lubricated, makes the funnel 114 a convenient location for grasping the catheter 110 to manipulate it. The funnel may be suitable for connection to a drainage bag, other tubing or any other appropriate apparatus. For example, in one embodiment the opening 120 defined in the free end 117 of the funnel may be large enough or otherwise adapted to receive a urine bag connector.

Near the end of the catheter tubing 112 opposite the funnel 114 is at least one radial eyelet (not shown). The eyelet provides fluid access to the central lumen 112A of the tubing 112. Adjacent the eyelet is a rounded tip 130 that provides a smooth surface to facilitate insertion of the tubing into a urethra. In some embodiments it may be desirable to include more than one eyelet.

Turning now to the catheter package assembly, it is shown generally at 64 in FIGS. 13-15. The package may include an elongated, hollow case 66 which has an axis A (FIG. 14) defined by a generally tubular wall 67. The inside or outside dimension of the tubular wall may have either circular or non-circular cross sections. The tubular wall 67 joins a bottom or end wall 69 that closes the bottom of the case 66. At the other end of the case the wall 67 terminates at a rim 68. The rim 68 defines an opening 70 at the top of the tubular wall 67. From the rim 68 and extending axially for a short distance the internal surface of the tubular wall 67 defines an internal seal face 71. When the catheter 110 is installed in the package 64, the internal seal face 71 engages the seal 118 of the funnel in an interference fit which provides a seal between the funnel and the package case 66.

The package 64 further includes a strap 72. The strap 72 is an elongated, flexible member which is fixedly attached to the tubular wall 67, preferably at or near the rim 66, by a living hinge 74. The other end of the strap 72 mounts a cap 76. The cap is joined to the strap by a living hinge 78. It will be understood that while a living hinge is a convenient method of connecting the cap and strap, other types of hinges are possible. The underside of the cap carries a boss 80. The length of the strap and the size of the cap and boss are such that the cap 76 will engage the opening 120 of a funnel 114 installed in the case 66. Thus, the cap does not engage the case 66, rather it is releasably engageable with the body portion 116 of the funnel 114.

When the cap is closed on the funnel, the boss 60 leads into the opening 120 in the free end of the funnel 114, producing contact between the boss and the internal wall of the funnel. This creates an interference fit and a seal between the boss and the internal surface of the funnel.

In the embodiment of FIGS. 13-15 a gel grommet 90 is placed inside the tubular wall 67 of the case 66 near the opening 70. The gel grommet 90 has a wall 92 whose external dimensions matches the internal dimensions of the wall 67 and are just slightly less than the internal diameter of the case 66. Thus, the grommet fits closely within the case 66. The ends of the wall 92 each carry a radially-disposed washer 94 with a central aperture 96 therein. The aperture 96 is sized to permit passage of the catheter tubing 112. The grommet is filled with a lubricating gel. The grommet may be made of a suitable silicone material.

Cooperation between the catheter 110 and package 64 is illustrated in FIGS. 14 and 15. To install the catheter in the package the catheter tubing 112 enters the case 66 through the opening 70. The inside dimension of the tubular wall 67 is greater than the outside diameter of the tubing 112 so the tubing fits in readily. There is a somewhat tighter fit between the tubing 112 and the washer apertures 96 but the tubing still has a small enough outer diameter to fit past the grommet. However, the inside dimensions of the opening 70 are slightly less than the outside dimensions of the funnel body portion 116. Thus, while the seal 118 of the funnel 114 will enter the case 66 in an interference fit, the remainder of the funnel will not. Accordingly, the body portion 116 of the funnel remains external to the case 66.

Once the catheter tubing 112 is inside the case 66 and the funnel seal portion 118 is snug against the seal face 71, the strap 72 may be rotated 90° about the hinge 74 to place the strap in a position where it is adjacent the funnel body 116 and generally parallel to the case axis A. Then the cap 76 is rotated 90° about the hinge 78. This will allow the boss 80 to fit in the funnel opening 120. The cap 76 and strap 72, together with the interference fit between the seal 118 and case 66, retain the catheter 110 in the package 64.

When the catheter is to be used, a user flips the cap 76 off of the funnel and grasps the outer surface of the funnel with one hand and the case 66 with the other hand. A gentle tilting, twisting or pulling of the funnel relative to the case will dislodge the funnel from the case and allow the user to withdraw the catheter from the case. In the withdrawal process the majority of the tubing 112 passes through the gel grommet 92. As it does so the tubing will become coated with the lubricant. Once the catheter is entirely removed from the case it will be almost completely coated with lubricating gel and thus ready for use.

The gel lubrication of the device will significantly reduce the overall cost of the product. Also, the package is reclosable and allows for carrying the catheter after use for later disposal without any leakage or odor.

Several alternate embodiments of the catheter funnel are shown in FIGS. 16-21. The first form of catheter having a funnel is shown at 110 in FIGS. 16-17. It has an elongated, hollow tubing 112 attached at one end to a hollow funnel 114. As before, the tubing and funnel each define a central lumen therein. The tubing lumen 112A can be seen in FIG. 16. Near the end of the tubing 112 are a pair of radial eyelets 128. The eyelets provide fluid access to the central lumen 112A of the tubing 112. Adjacent the eyelet is a rounded tip 130 that provides a smooth surface to facilitate insertion of the tubing into a urethra.

The funnel 114 has an upper body portion 116 and a lower seal portion shown generally at 118. The upper or free end 117 of the body portion 116 defines a funnel opening 120. As in the previous embodiment, the funnel 114 generally has an outer dimension greater than that of the tubing 112. Further details of the seal 118 at the lower end of the funnel include a beveled lower portion 122 joining a cylindrical section 124 on which is mounted an O-ring 126. The O-ring 126 engages the interior of the package case in an interference fit that seals the funnel to the case. The beveled lower portion 122 assists in guiding the seal portion 118 into the case. Other embodiments for the seal portion are possible as each of the components described above may not be necessary in all instances.

Figure 16:
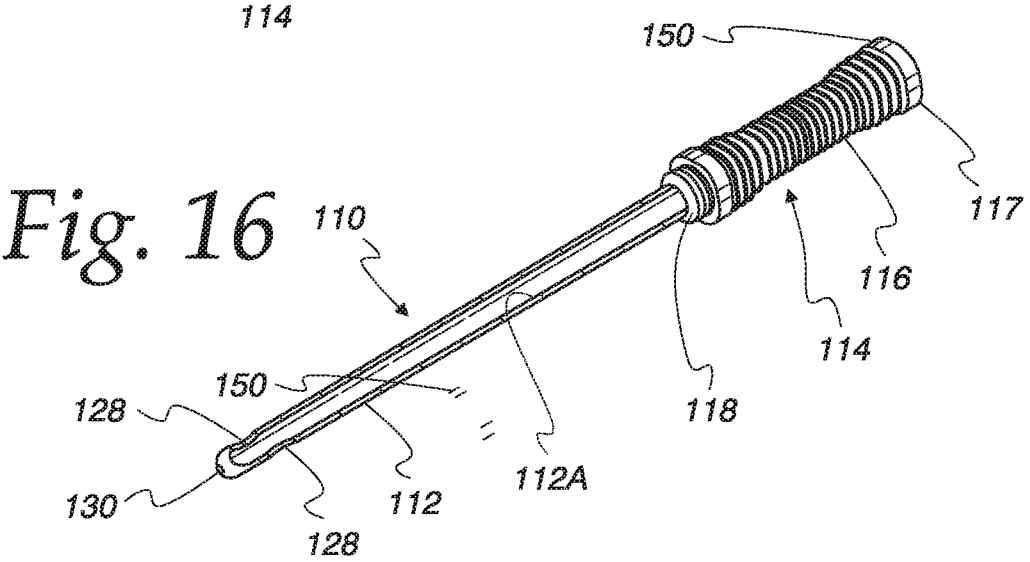
FIG. 16 is a perspective view of a catheter of the present disclosure with an alternate form of a funnel and the catheter tubing shown in section.
Figure 17:
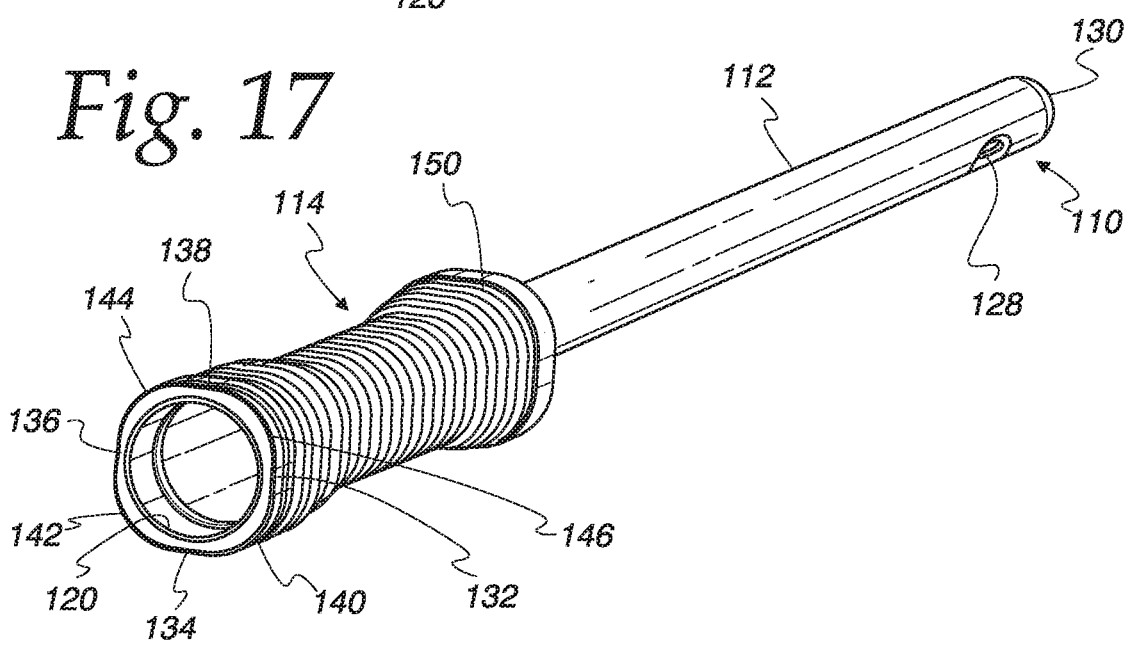
FIG. 17 is a perspective view, somewhat enlarged, looking into the open end of the funnel of the catheter of FIG. 16.

The upper body portion 116 in FIGS. 16-18 may be characterized by a cross section having a circular internal diameter and an external shape that varies from square ends to a circular middle. More particularly, the external surface may have two tactile rings 150 and the ends of the funnel. The tactile rings have a generally square cross section, as seen in FIG. 18A. Adjacent sides of the tactile rings are joined by arcuate corners of comparatively large radius, thus providing rather soft corners instead of the sharp corners of a true square shape. Nevertheless, the flat sides have a width (or height depending on the orientation of the funnel) that is large enough to provide a clear tactile distinction between the sides and the corners. A user can readily distinguish the sides from the corners, thus providing a more secure grip on the funnel. Intermediate the tactile rings 150 the funnel has a generally circular cross section, as seen in FIG. 18B. Thus, the external shape gradually undergoes a metamorphosis along its length as the external shape modulates from square at one end to circular intermediate the ends and then back to square at the other end.

Looking at FIG. 17, it can be seen that internal diameter of the funnel is defined by the circular cross section of the funnel opening 120 and the funnel lumen 114A. The circular internal diameter may allow for attachment to standard drainage bags. The external shape of the tactile rings 150 of the funnel are defined by at least substantially flat sides 132, 134, 136 and 138. The pair of sides 132 and 136 are parallel to one another. Similarly, the pair of sides 134 and 138 are parallel to one another. Sides 132 and 134 are joined by arcuate corner portion 140. Sides 134 and 136 are joined by arcuate corner portion 142. Sides 136 and 138 are joined by arcuate corner portion 144. Sides 138 and 132 are joined by arcuate corner portion 146.

While the preferred arrangement of at least four substantially flat sides is shown, it will be understood that other arrangements are possible for the tactile rings, with the number of flat sides varying from one to several. For example, two spaced, parallel, at least substantially flat sides could be joined by arcuate sides.

FIG. 18 illustrates additional features that enhance the ability of the user to securely grip the funnel 114. These may include a series of ridges 148 on the external surfaces of the funnel body 116. The ridges are local protrusions from the external surface of the body 116. They may be spiral, like a screw thread, or they could be separate, individual rings, as shown here. As seen in FIG. 18 they could have a variable helix angle from one end of the funnel body to the other. The ridges may be formed from the same material as the funnel. Alternately, the ridges could be of a different material or different stiffness. That is, the ridges could be comparatively soft to improve grip while the funnel body would be stiff to prevent the funnel from collapsing when gripped.

FIG. 18 illustrates another grip enhancing feature in the form of the tactile rings 150 at each end of the funnel body 116. In this embodiment the tactile ring 150 is a portion of slightly increased external dimension compared to the ridges 148. The ring itself has a smooth surface to distinguish it from the ridged portion of the funnel. This tactile surface allows the user to feel when he or she is nearing the end of the funnel. As the funnel may be relatively short, this ring would indicate to the user if his or her fingers are nearing the funnel ends and thereby avoid accidental finger contact with the catheter tubing, which could result in contamination of the catheter tubing.

FIGS. 19 and 20 show another alternate configuration of a funnel 152. This funnel has a generally circular external diameter with a somewhat parabolic shape along its axial dimension. The external surface is generally smooth except where enlarged tactile rings 154 protrude near the ends of the funnel. The rings 154 are more pronounced than the ring 150 of the previous embodiment but they still provide the same indication to the user of approach to the end of the funnel.

Figure 21:
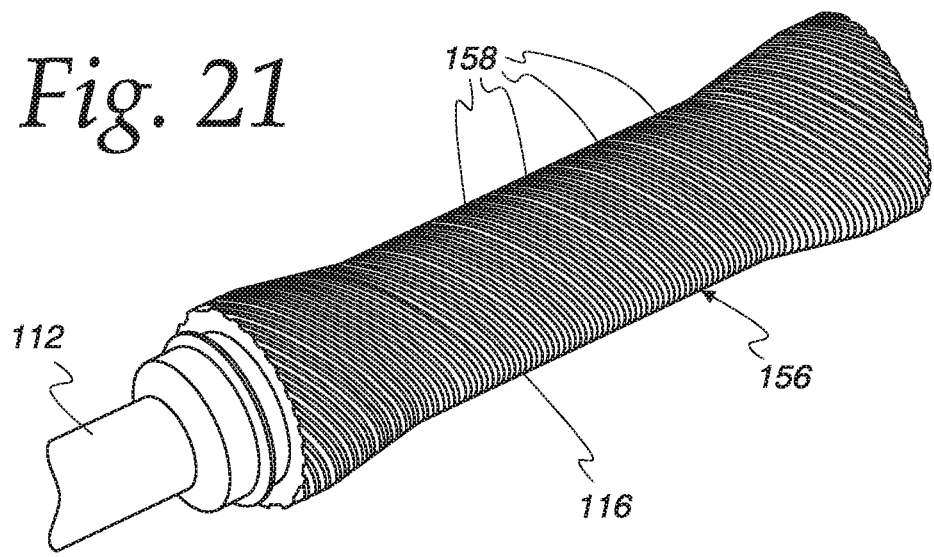
FIG. 21 is a perspective view of a further alternate funnel surface texture.

FIG. 21 shows still another variation of a funnel 156. In this version spiral ridges 158 are formed along virtually the entire axial extent of the funnel body. The ridges 158 could have different designs or orientations.

All of the embodiments of FIGS. 16-21 address the issue of gripping a catheter that has no sleeve and rely on gripping of the funnel for hygienic catheter use. In such situations it can happen that a user's fingers may slip off the funnel and contaminate the catheter tubing or come into contact with urine. The designs of the present disclosure aid in funnel grip and positioning and limit the potential for slippage. They permit the user to use his or her sense of touch during use so they can feel when they are nearing the end of the funnel. The ridges will help limit slippage if the funnel is wet due to hydration or other causes. The ridges give the user a sense of a more secure grip. The tactile ring will also help during attachment to a drainage bag as it is slightly raised, giving an improved grip during attachment.

Figure 22:
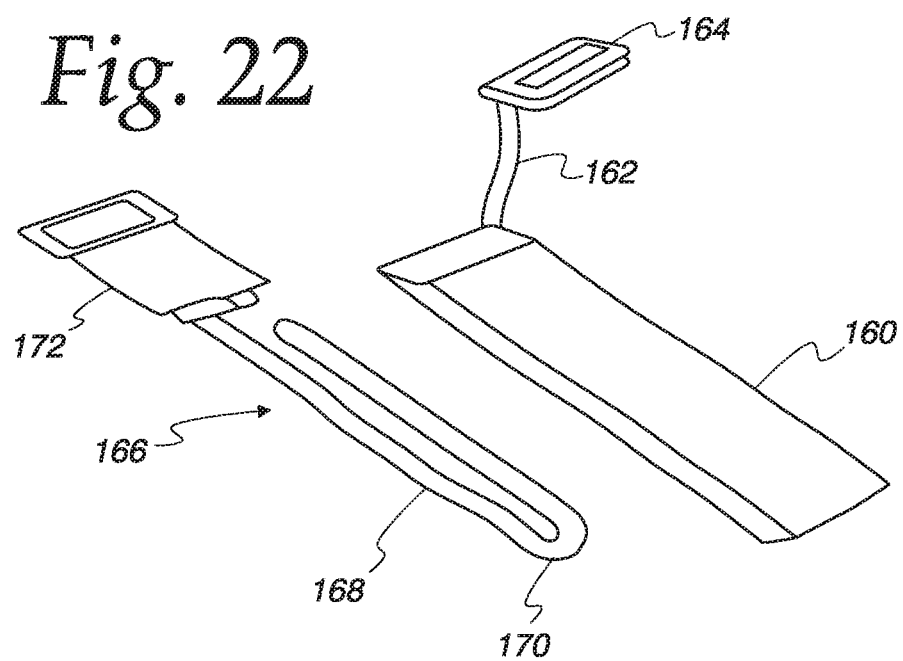
FIG. 22 is a perspective view of an alternate embodiment of the package for a male catheter.

FIG. 22 illustrates another alternate embodiment of the present disclosure. This is a package having a case 160, a strap 162 and a cap 164. This case may have a rectangular cross section and does not include a gel grommet, but it is otherwise similar to the package of FIGS. 13-15. This particular package may be particularly well suited for a male catheter, shown generally at 166. The male catheter tubing 168 is longer than that of a female catheter. The extra length creates packaging challenges. The present disclosure addresses this problem by folding the tubing at fold 170. The catheter is placed in the case in a folded position to minimize the overall package size. The outer part of the grip 172 is slideable along the catheter tubing to be used as a gripper and enhance hygienic benefits.

FIGS. 23-29 illustrate a sequence of steps for assembling a package 174 according to the present disclosure. This particular embodiment utilizes a hydrating medium in the form of a wick 176 or a sachet. The wick may be, for example, a fabric strip, an absorbent paper strip, an absorbent open-celled foam strip or anything else that will emit a vapor. The method then also advantageously includes wetting the wick with an aqueous liquid prior to inserting it into the package 174 to thereafter produce a water vapor atmosphere within the sealed cavity to activate the hydrophilic coating. The wick is placed in the case 178 prior to the installation of the catheter. The wick in this embodiment is basically a rectangle that is partially folded into a shape with two portions perpendicular to one another. This allows it to bear against the inside surface of the case walls, which in this embodiment have a generally square cross section, although the case walls could have a different cross section, such as a circular cross section. Water vapor emanating from the wick 176 will lubricate the coating on the catheter tubing.

FIG. 23 illustrates the package generally at 174. This embodiment has a case 178 which has a generally square cross section. The case 178 terminates at a rim 180 which defines an opening 182. The case 178 is sized to receive a catheter tubing and an adaptor or liner as will be described below. The body portion of the catheter funnel will remain on the exterior of the case. The package 174 has a strap 184 which is attached at one end to the case 178 at a hinge 186. A cap 188 is attached to the other end of the strap 184 by a second hinge 190. Hinges 186 and 190 are preferably living hinges although it could be otherwise. The cap 188 includes a boss 192. The cap 188 may further include a tab 194 extending from an edge of the cap to assist a user in removing the cap from a catheter funnel.

Figure 25:
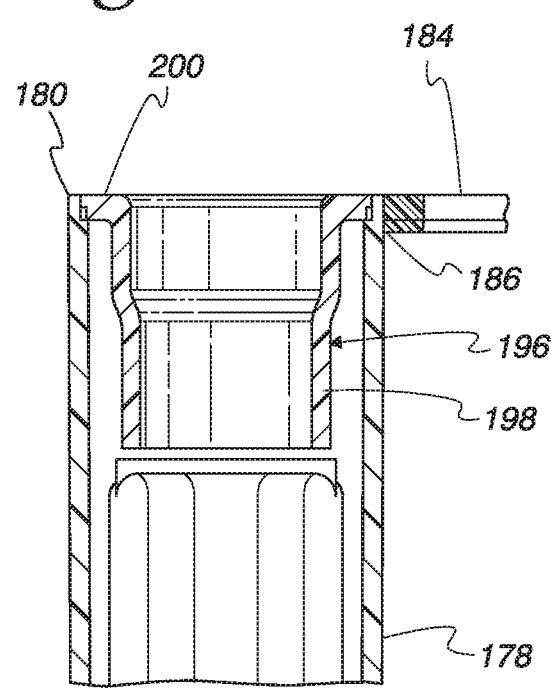
FIG. 25 is a section through the top of a package case with an adaptor installed therein, on an enlarged scale.

The first step in the assembly process is installation of the folded sachet 176 into the case 178, as illustrated by arrow B in FIG. 23. The second step in the assembly process is shown in FIG. 24 and entails installation of an adaptor 196 into the opening 182 of the case 178. The adaptor is moved in the direction of arrow C to form an adaptor/case sub-assembly. The adaptor has, in this case, a rectangular, hollow ferrule 198 that terminates at its upper end at a flange 200. The flange engages the internal surface of the case wall in a press fit as seen in FIG. 25.

Figure 26:
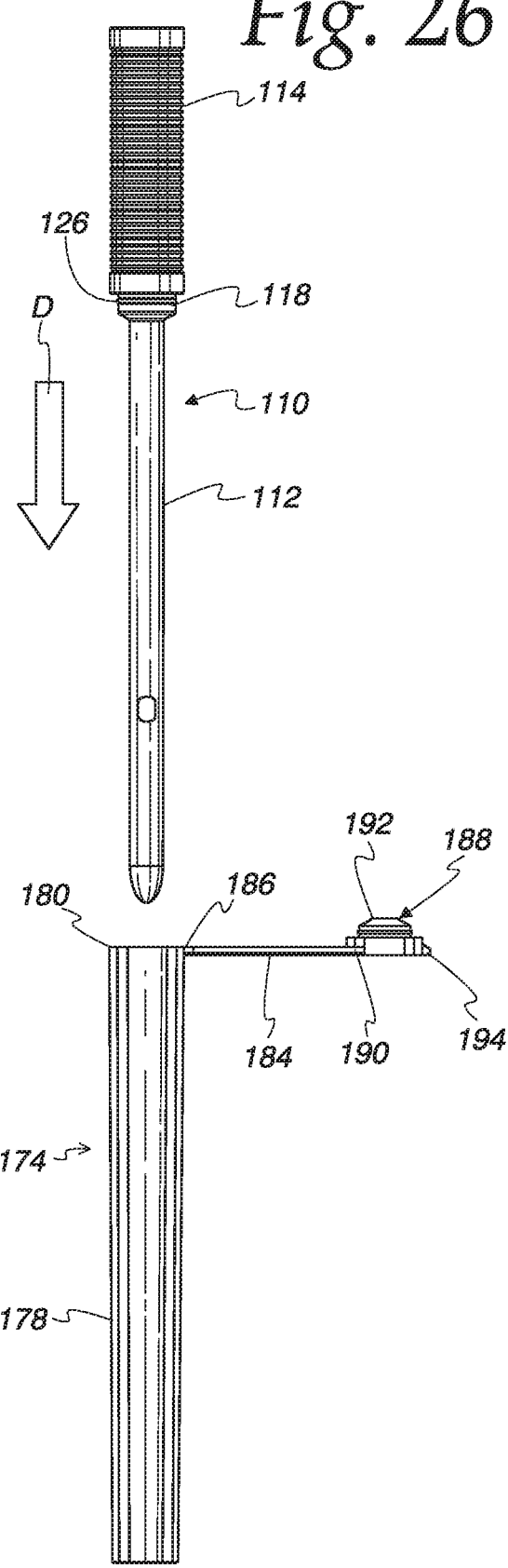
FIG. 26 is a side elevation view of a third step in an assembly process for a package hydrated by a sachet, illustrating installation of a female catheter into the package case and adaptor.
Figure 27:
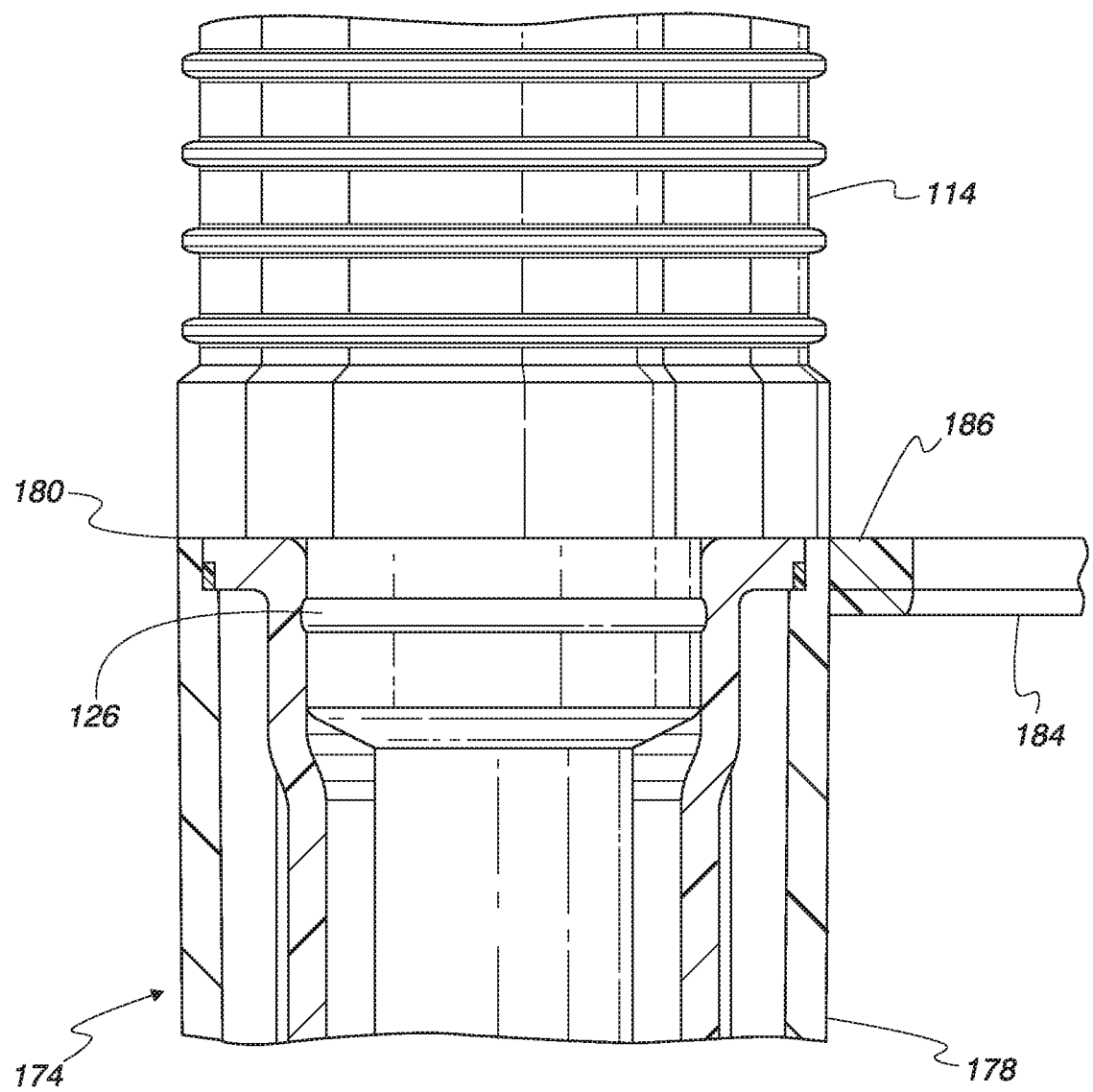
FIG. 27 is a section through the top of a package case with an adaptor and catheter installed therein, on an enlarged scale.

The third step in the assembly process is shown in FIG. 26 and entails installation of a catheter into the adaptor/case sub-assembly. The catheter may be similar to that shown at 110 in FIGS. 16-21. The seal portion 118 of the catheter is inserted into the ferrule 198 of the adaptor as shown by arrow D in FIG. 26. The O-ring 126 of the funnel seal portion 118 engages the internal surface of the ferrule in a press fit to seal the funnel to the adaptor. This is best seen in FIG. 27.

Figure 28:
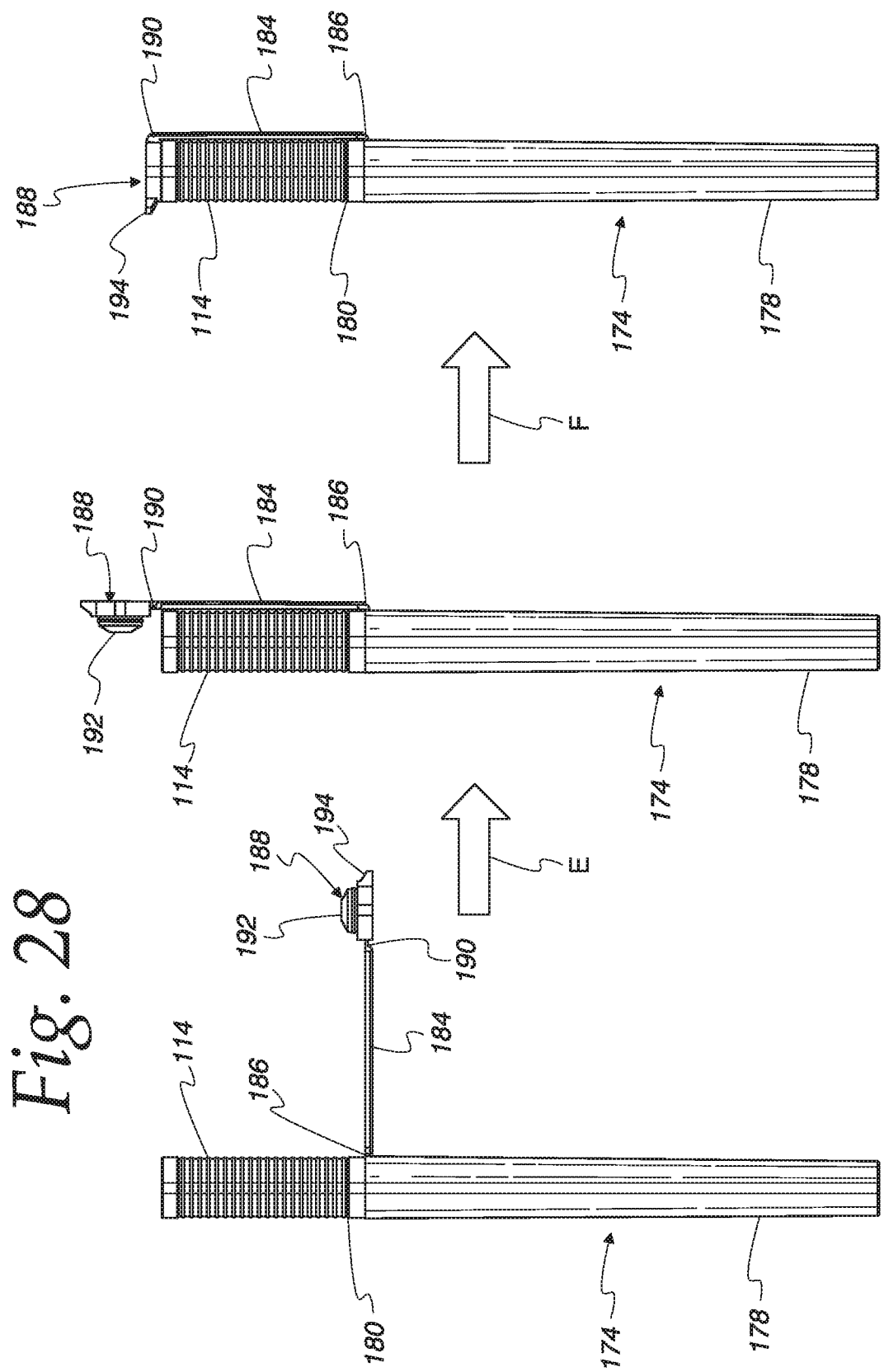
FIG. 28 is a side elevation view of a fourth step in an assembly process for a package, illustrating installation of the cap onto the catheter funnel.

Once the catheter 110 is in the adaptor/case sub-assembly the package will be in the state shown at the left hand side of FIG. 28. The cap can then be closed as shown in the successive middle and right hand views of FIG. 28. First the strap 184 is folded up 90° about hinge 186 as indicated by arrow E. This places the strap 184 essentially parallel to the funnel body 116 with the cap 188 located above the free end 117 of the funnel body. Then, as shown by arrow F, the cap 188 is folded 90° about hinge 190. This places the boss 192 of the cap inside the funnel opening 120 to seal the funnel lumen and retain the catheter in the package.

Figure 29:
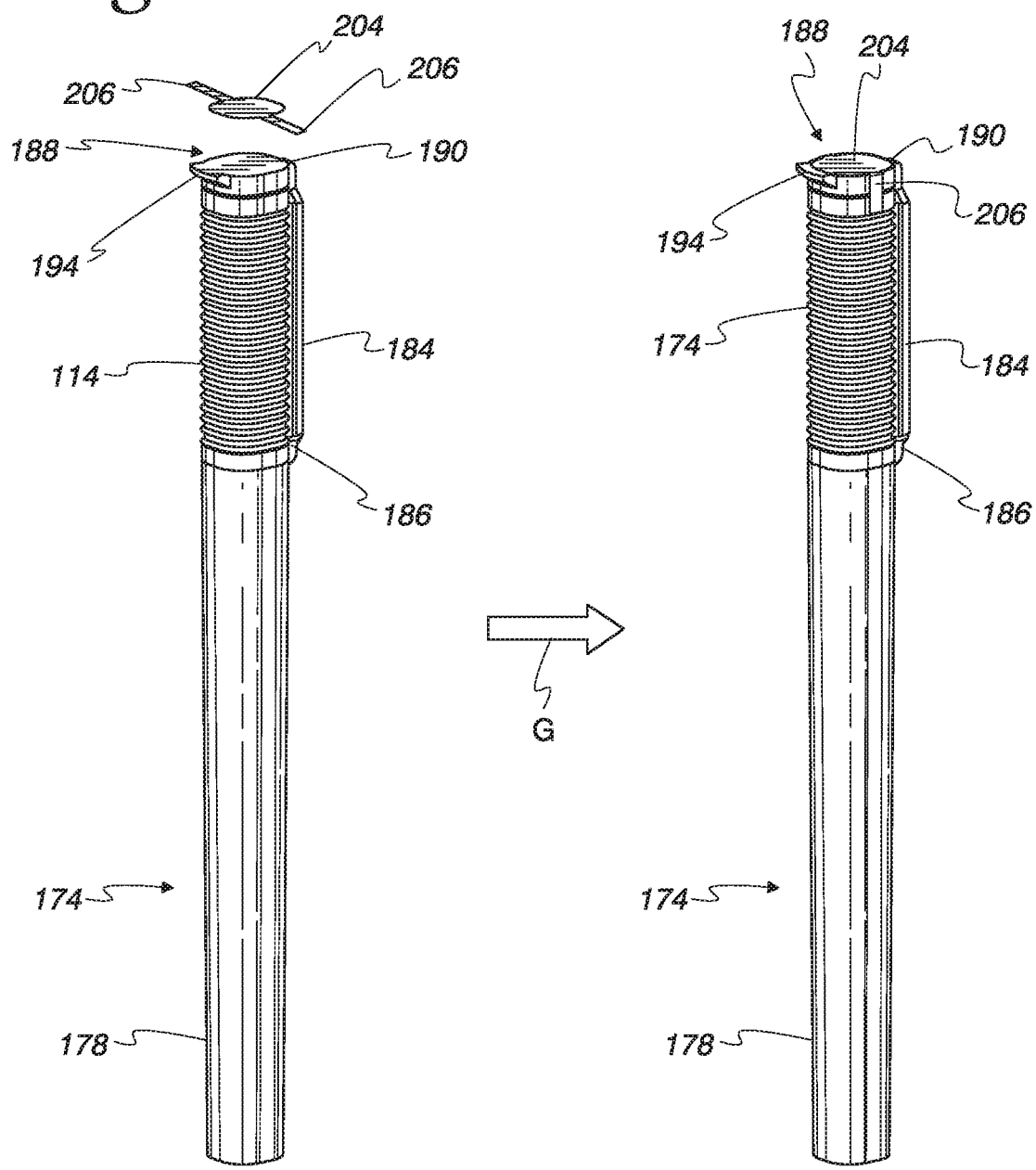
FIG. 29 is a perspective view of a fifth step in an assembly process for a package, illustrating installation of a tamper evident label onto the cap.

The final assembly steps are shown in FIG. 29. Here a tamper evident label 204 is placed over the cap 188. The label may have tabs 206 that are long enough to extend down onto and engage the funnel as indicated by arrow G. If the cap 188 is opened these tabs will break, indicating a post-assembly opening of the cap. The right hand view of FIG. 29 shows the complete assembly of the package.

FIGS. 30-35 illustrate an alternate embodiment of the catheter package assembly 208 of the present disclosure. This version uses a different hydrating method from the sachet 176 used in FIGS. 23-29. Instead of the sachet, about 1.5 ml of liquid water is added to the case and a liner is inserted into the case to separate the catheter tubing from the liquid water. The liner is an elongated tube that fits within the case. The liner has an upper end that engages the internal walls of the case in a press fit. Once that press fit is established the liner and case form a liner/case sub-assembly. That sub-assembly presents a structure that it is ready to receive a catheter.

Figures 30, 31:
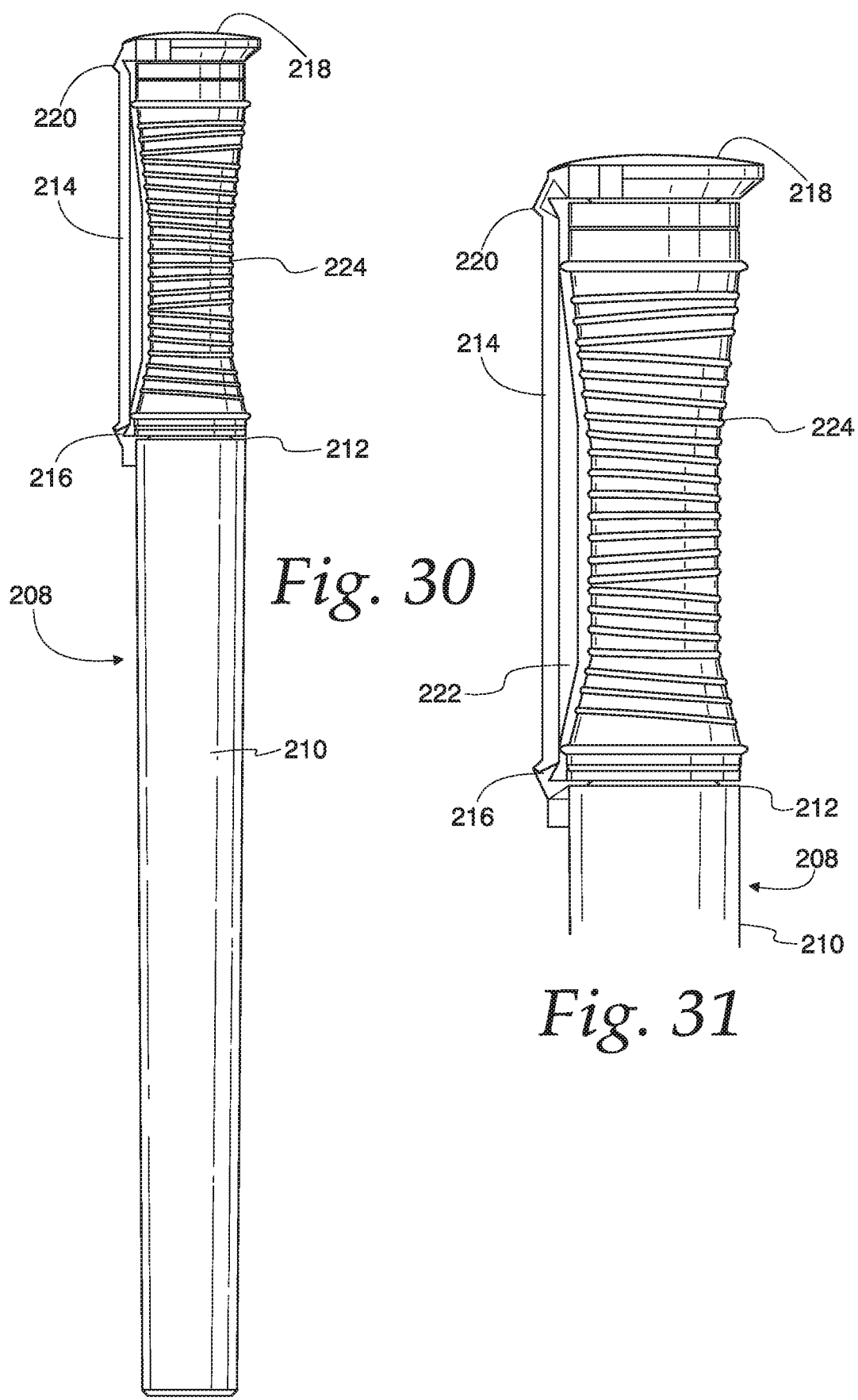
FIG. 30 is a perspective view of a further alternate embodiment of a catheter package assembly of the present disclosure, with the catheter and cap both in their installed positions in a package hydrated by liquid water.
FIG. 31 is a side elevation view, on an enlarged scale, of the top of the case, the funnel and the cap of the catheter package assembly of FIG. 30.

FIGS. 30-31 illustrate the external portions of the catheter package assembly 208. It includes a case 210 that is similar to the previous cases in that it is a hollow tube. In this embodiment, however, the case has an outer cross section with generally flat sides joined by broadly radiused corners. The internal cross section of the case 210, however, is circular. The case 210 terminates at a rim 212 which defines an opening. The case 210 is sized to receive a catheter tubing and the seal portion of a catheter funnel, as well as a liner as will be described below. The body portion of the catheter funnel will remain on the exterior of the case.

The case 210 further includes a strap 214 which is attached at one end to the case at a hinge 216. A cap 218 is attached to the other end of the strap 214 by a second hinge 220. Hinges 216 and 220 are preferably living hinges although they could be otherwise. The strap 214 includes a longitudinal rib 222 that extends generally perpendicular to the main body of the strap, thereby producing a T-shaped cross section in the strap. The free edge of the rib 222 has a shape that closely conforms to the contour of the funnel's exterior surface. This construction not only strengthens the strap but it also leaves little or no gap between the strap and the funnel. This prevents entanglement of the strap with items that might otherwise be inserted between the strap and the funnel.

Figures 32, 33:
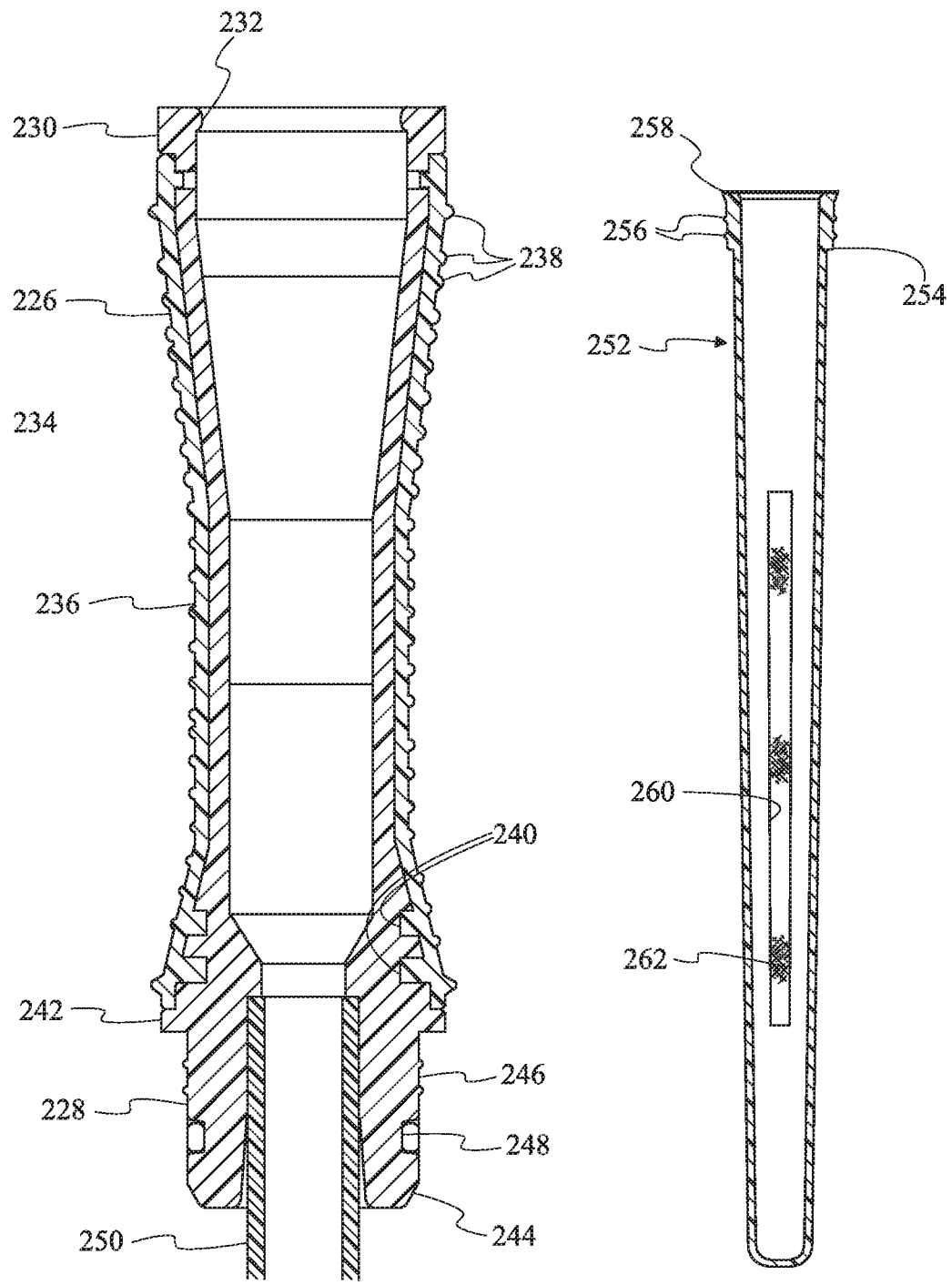
FIG. 32 is a section through the funnel and a top portion of the tubing of the catheter shown in FIG. 31.
FIG. 33 is a longitudinal section through a liner, which fits inside the case of the package assembly of FIG. 30.

The funnel of a catheter is also visible at 224 in FIGS. 30-31. Details of the catheter construction are shown in FIG. 32. As in previous embodiments the funnel 224 has an upper body portion 226 and a lower seal portion generally at 228. The upper or free end 230 of the body portion 226 defines a funnel opening 232. While the upper body portion 226 is shown having a gently curved outer surface that is somewhat parabolic in nature, it will be understood that other exterior shapes for the funnel are possible. In this case both the internal and external cross sections of the funnel are circular throughout the length of the funnel. Thus, the seal portion 228 fits into the opening at the rim 212 of the case 210 without the need for an adaptor.

The upper body portion 226 in the illustrated embodiment may be a two-shot molded component. In such embodiment, the first or internal shot is preferably a relatively rigid material such as ABS or a similar alternative. It forms the seal portion 228 and the body of the funnel 234. The second or external shot is preferably a softer material such as TPE and forms the gripping surface 236 of the funnel, including ridges 238. Interlocking grooves and ribs at 240 near the bottom of the second shot help retain the gripping surface in position on the body. The extreme lower edge of the gripping surface overlies a flange 242 at the top of the seal portion 228. The flange adjoins the top land of the case's rim 212 when the catheter is installed in the case, as will be explained below.

Further details of the seal portion 228 include a beveled lower portion 244 joining a cylindrical section 246. There is a groove 248 in the cylindrical section for receiving an O-ring as shown below. The beveled lower portion 244 assists in guiding the seal portion 228 into the case as explained below. A bore through the center of the seal portion receives the top portion of the catheter tubing 250 in a press fit.

Turning now to FIG. 33, a liner 252 is shown. The liner may be a relatively rigid plastic such as LDPE or HDPE. The liner is generally a hollow tube. At its upper end there is a seat portion 254 of slightly increased outside diameter compared to the remainder of the liner's tube. A pair of interference ribs 256 may be formed on the seat 254. At the top edge there is, for example, a crab claw seal 258. The walls of the liner have formed therein one or more passages or windows 260 in it. The windows will be covered with a patch 262 of liquid impermeable/vapor permeable material such as, but not limited to, calcium carbonate. The patches 262 will allow passage of water vapor (for hydration of the catheter) but will block passage of liquid water droplets. The patch might be heat sealed around the perimeter of the window.

Figure 34:
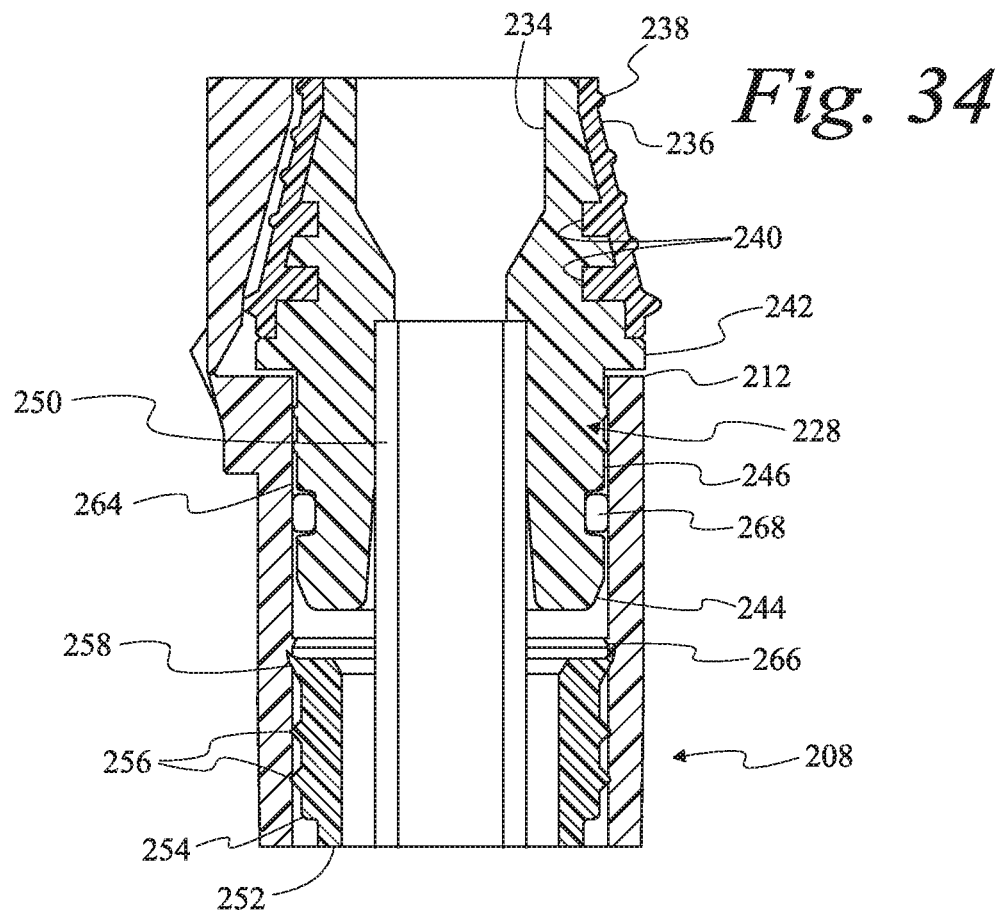
FIG. 34 is a longitudinal section through the top of the liner, catheter tubing and case, and the bottom of the funnel.

FIG. 34 illustrates the internal construction of the catheter package assembly 208 after installation of the liner 252 and catheter funnel 224. It will be noted that the internal surface of the case 210 has upper and lower undercuts 264, 266 formed therein. The upper undercut 264 cooperates with an O-ring 268 disposed in the groove 248. The lower undercut 266 cooperates with the crab claw seal 258 on the liner 252 resist withdrawal of the liner from the case 210. Together with the interference ribs 254, the O-ring 268 and crab claw seal 258 seal the top of the case and prevent release of liquid water or water vapor from the case.

Figure 35:
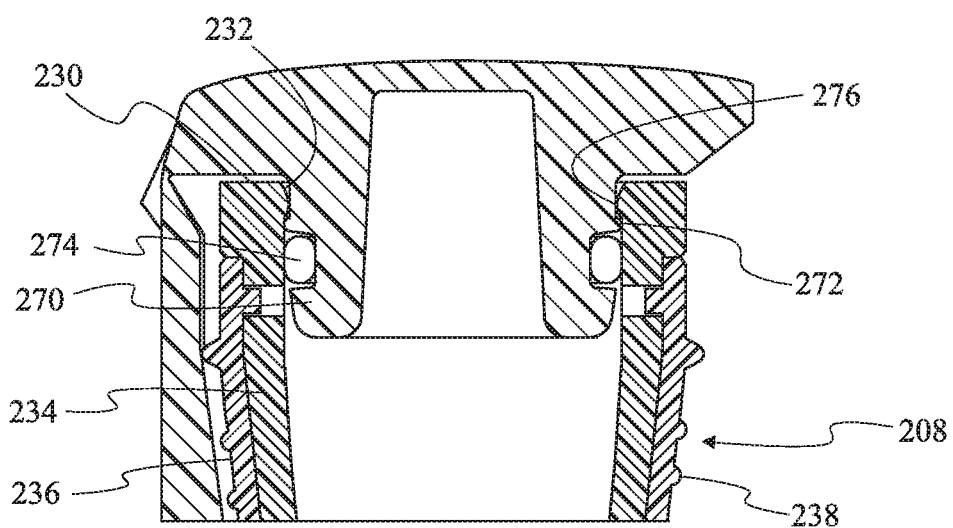
FIG. 35 is a longitudinal section through the top of the funnel and the cap.

FIG. 35 illustrates details of the engagement of the cap 218 and the body portion 226 of the funnel 224. The cap includes a boss 270. The boss has a bump 272 just above a groove that receives an O-ring 274. On the internal wall surface of the funnel, just inside the opening 232 there is a bump undercut 276. The bump 272 and bump undercut 276 cooperate with one another and with the O-ring 274 to seal the top of the funnel and prevent release of water vapor or the entry of contaminants.

Among the advantages of the packaging assembly with a liner is the liner is relatively easy to install in the case. The liner separates liquid water from the catheter tubing while allowing water vapor to maintain the coating on the tubing in a lubricious condition. When the time comes for the catheter to be put to use, a user can simply flip open the cap 218, removing the boss 270 and cap 218 from engagement with the funnel 224. The strap 214 can be pressed aside slightly to permit the user to grasp the funnel and pull the catheter out of the package. Due to the hydration the catheter is ready for immediate use.

A further alternate embodiment form of a hydrating mechanism is to place liquid water in the case 178 alongside the catheter. This would negate the need for hydration via either a sachet or a hydration liner.

It will be noted that the product signifies the correct orientation for opening such that there will not be spillage upon opening the product. There can be a tamper-evident label joining the cap to the funnel. Another advantage is the package is reclosable and allows for carrying the product after use for later disposal without any leakage or odors.

As mentioned above, it is possible to manufacture the strap as a separate member from the case and then attach the strap to the case at a hinge. One embodiment of such a structure is shown in FIGS. 36-41. Here a catheter funnel 278 is shown installed in a case 280, only the top portion of the case being shown in FIGS. 36-38. The case has a pair of hinge blocks 282 formed on the exterior walls of the case, on opposite sides thereof. Each hinge block 282 has a U-shaped socket 284 cut in a side of the hinge block. A pin 286 is mounted for rotation in each socket 284. The sockets may be arranged to permit the pins to be twisted into the sockets. Flexibly interengaging portions of the hinge block retain the pins. Each of the two pins 286 is fixed to a leg 288, on an inwardly facing surface thereof. There are two legs 288, each leg carrying one of the pins 286. Together the legs 288 define a stirrup at the bottom of a semi-cylindrical strap 290. A cap 292 is hinged to the stop of the strap 290. The cap is releasably engageable with the funnel as in the embodiments shown above. The cap 282 may have a tamper evident feature 294 connecting it to the strap 290 for indicating whether the cap has been opened.

Figures 36, 37:
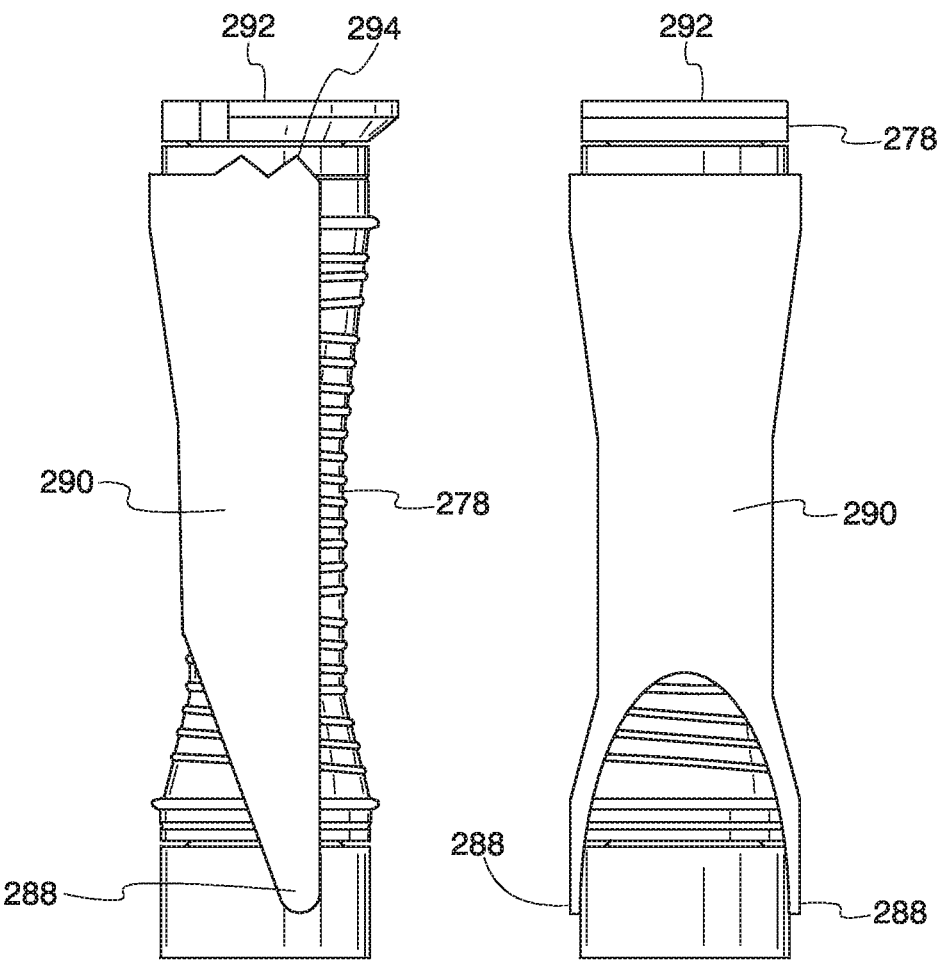
FIG. 36 is a side elevation view of a funnel installed in the top portion of a case, showing an alternate embodiment of the strap.
FIG. 37 is a front elevation view of the strap, case and funnel of FIG. 36.
Figures 38, 39:
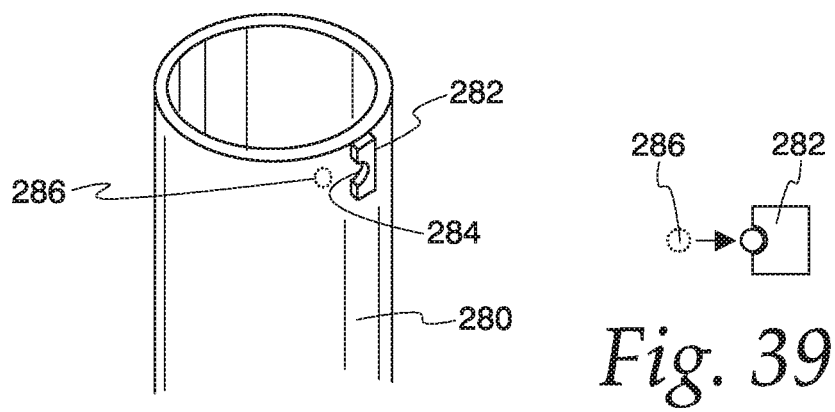
FIG. 38 is a perspective view of the top of the case, with the catheter and strap removed to show the hinge block.
FIG. 39 is a diagrammatic side elevation view of the hinge block and a hinge pin movable into the hinge block.
Figures 40, 41, 42:
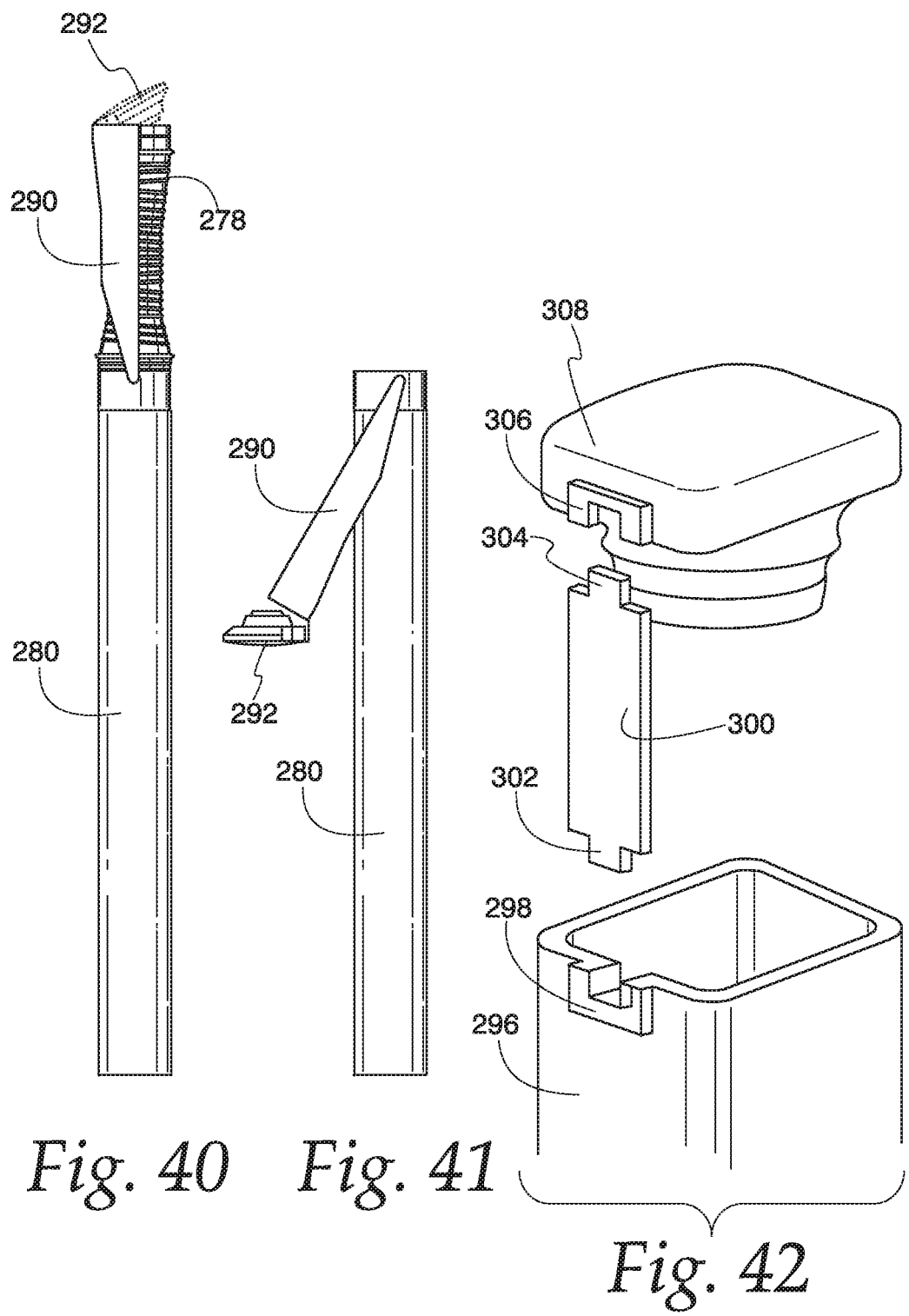
FIG. 40 is a side elevation view of a catheter package assembly according to FIG. 36 with a partially open cap shown in phantom lines.
FIG. 41 is a view similar to FIG. 40 with the cap and strap fully open and the catheter removed from the case.
FIG. 42 is an exploded perspective view of a further alternate embodiment of a strap and hinge construction.

FIGS. 36 and 40 show the strap installed on the funnel 278, with a partially opened cap 292 shown in phantom lines in FIG. 40. FIG. 41 shows how the strap 290 would pivot about the pins to a fully open position. The catheter has been withdrawn from the case in FIG. 41.

FIG. 42 illustrates another embodiment having a strap initially formed separate from the case and subsequently attached at a hinge to the case. In this embodiment the case 296 has a hinge receptacle 298 at the upper edge of the case. The strap 300 has a tongue 302 that is engageable with the receptacle 298 for pivoting motion therein. Another tongue 304 at the top of the strap 300 engages a receptacle 306 which is similar to receptacle 298. It permits the cap 308 to pivot on the outer end of the strap 300. In each case the tongue snaps into pivotable engagement with the receptacles. If desired, the attachment of the strap could be done after installation of the funnel and cap.

Figure 45:
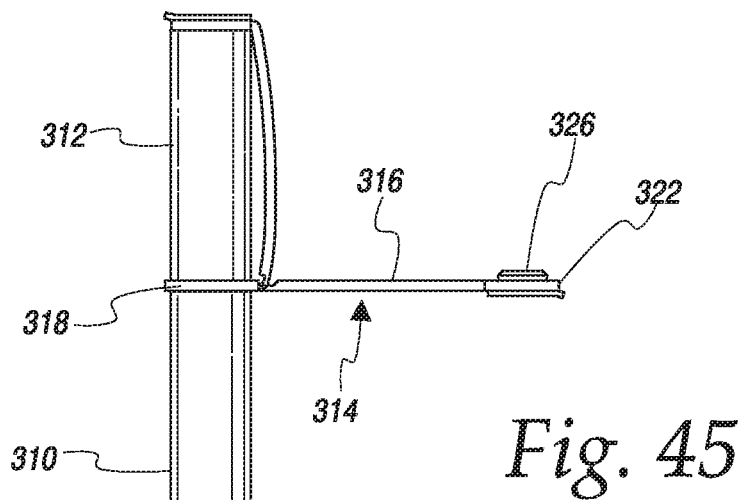
FIG. 45 is a side elevation view of a catheter package assembly having the strap of FIGS. 43 and 44, with the strap shown in both open and closed positions.
Figure 43:
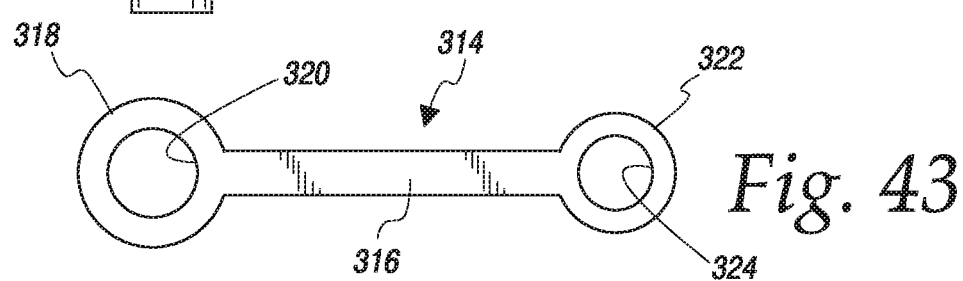
FIG. 43 is a top plan view of yet another alternate embodiment of a strap.
Figure 44:
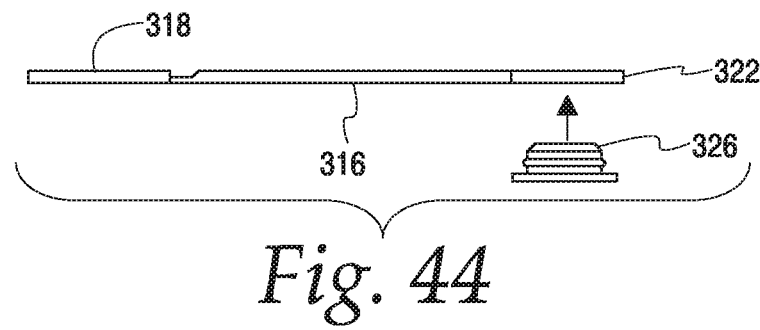
FIG. 44 is an exploded side elevation view of the strap of FIG. 43 plus a cap.

An additional embodiment of a strap separate from the case is shown in FIGS. 43-45. Here a case 310 receives a funnel 312 in a manner similar to the embodiments described above. A strap 314 has an elongated body member 316. Attached to one end of the body 316 is an anchor ring 318. The anchor ring has a central opening 320 of a diameter that allows the anchor ring to fit snugly about the top of the case 310. Alternately, the top of the case may have a groove for receiving the anchor ring. The end of the strap 314 opposite the anchor ring has a second ring 322 with an aperture 324 therein. The aperture receives a cap 326. The body member 316 has sufficient flexibility to permit it to be folded back on itself as shown in FIG. 45 to permit the cap 326 to be inserted into the opening of the funnel 312. A user can flip the cap off the funnel to allow extraction of the funnel and catheter tubing from the case 310.

An alternative arrangement for the strap 314 is to have a hyperbolic funnel, with flared ends as in FIGS. 30-32 and size the anchor opening 320 fit around the narrower parts of the funnel at or near its longitudinal center. The opening permits the anchor to slide up and down the funnel somewhat but it does not fall off the funnel due to the flared funnel ends.

Figure 46:
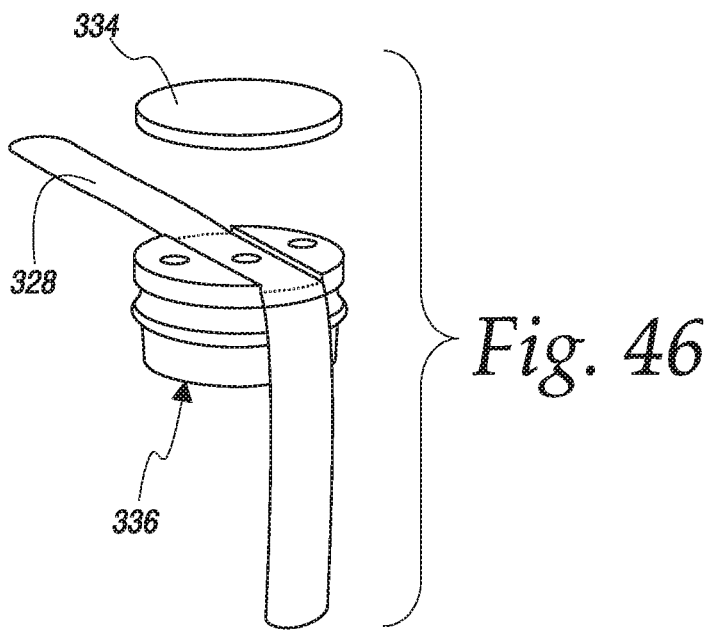
FIG. 46 is an exploded perspective view of a still further embodiment of a strap and cap arrangement wherein the strap takes the form of a label.
Figure 47:
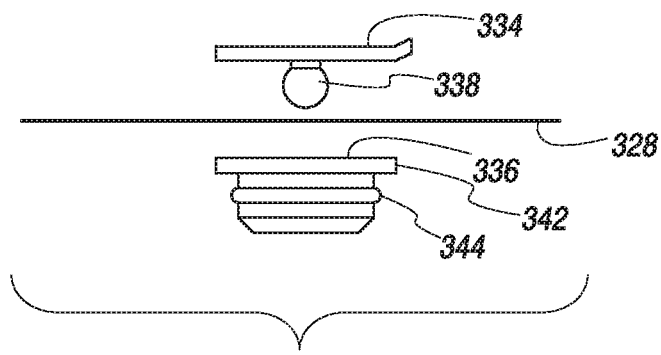
FIG. 47 is an exploded side elevation view of the strap and cap of FIG. 46.
Figure 48:
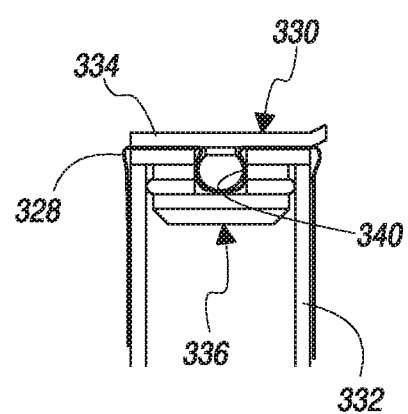
FIG. 48 is a longitudinal section through the strap and cap of FIG. 46.

Until now the various illustrated embodiments of the strap contemplate the strap being a molded plastic part. The strap could also be an elongated piece of label stock attached to the cap and case in various manners as will now be illustrated. FIGS. 46-48 show a version with a mechanical attachment of the label 328 to the cap 330 and an adhesive attachment of the label to the case. A portion of the funnel is shown at 332 in FIG. 48. The cap has two pieces, a cover 334 and a seat 336. The underside of the cover 334 carries a spud 338. The seat has a socket 340 that receives the spud 338. The seat also has a flange 342 on its upper edge. An O-ring seal 344 surrounds the body of the seat. Assembly of the label 328 to the cap 330 is shown in FIG. 47, with the label disposed between the cover 334 and seat 336. The label may have a perforation which the spud 338 penetrates to extend through the label. The spud then snaps into the socket 340 of the seat 336, locking the cover and seat together with the label secured between them. The label extends past the funnel 332 to a point adjacent the case (not shown). That portion of the label will have an adhesive that is secured to the outer surface of the case. The label is sufficiently flexible to allow bending of it when the user flips the cap 330 off the funnel 332. While the label can be readily flexed away from the funnel, the label has sufficient tensile strength to prevent stretching it lengthwise.

Figure 49:
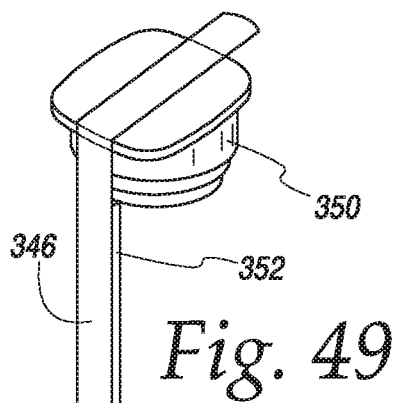
FIG. 49 is a perspective view of another alternate embodiment of a strap and cap with the strap in the form of a label.
Figure 50:
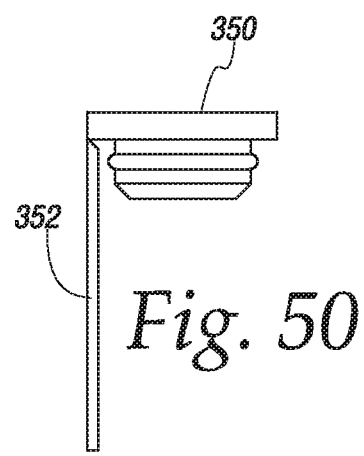
FIG. 50 is a side elevation view of the cap used in FIG. 49.

FIGS. 49 and 50 illustrate an alternate version of a label 346 as a strap. The label is adhesively attached to the case 348 and to the cap 350. The cap may include a depending leg 352 extending from one side thereof. However, this leg is not attached to the case 348. It fills any space between the label and the funnel. If there is adhesive throughout the length of the label the leg 352 also prevents the label from sticking to the funnel. The label may extend somewhat beyond the edge of the cap so that it can be grasped by a user to assist in flipping the cap off the funnel.

Figure 51:
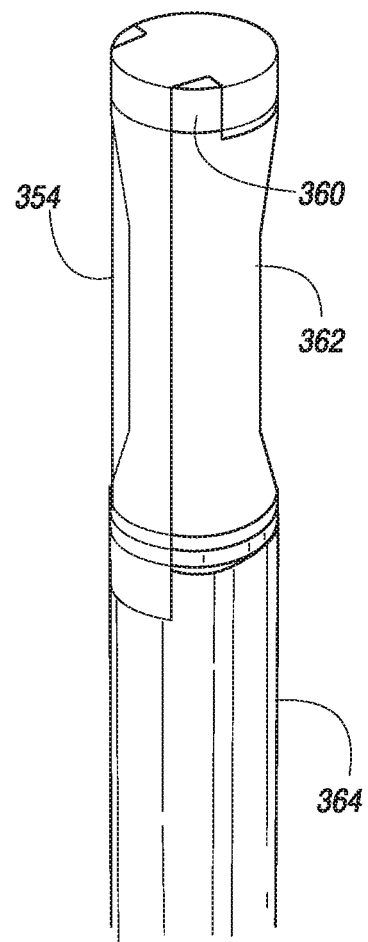
FIG. 51 is a perspective view of a catheter package assembly having a still further alternate embodiment of a strap in the form of a label.
Figure 52:
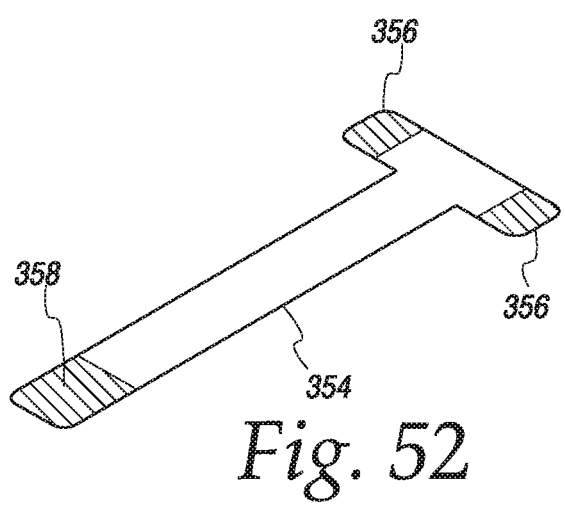
FIG. 52 is a perspective view of the underside of the label used in the catheter package assembly of FIG. 51.

FIGS. 51 and 52 show still another alternate form of a label 354 as a strap. The strap has wing areas at 356. These are covered on the underside with adhesive as shown by the hatching. A similar adhesive area is at 358 near the bottom of the strap. A cap 360 fits in the funnel 362. The wings 356 fold down over the cap and the label extends past the funnel 362 to the case 364, where the adhesive zone 358 adheres the label 354 to the case.

Figures 53, 54, 55:
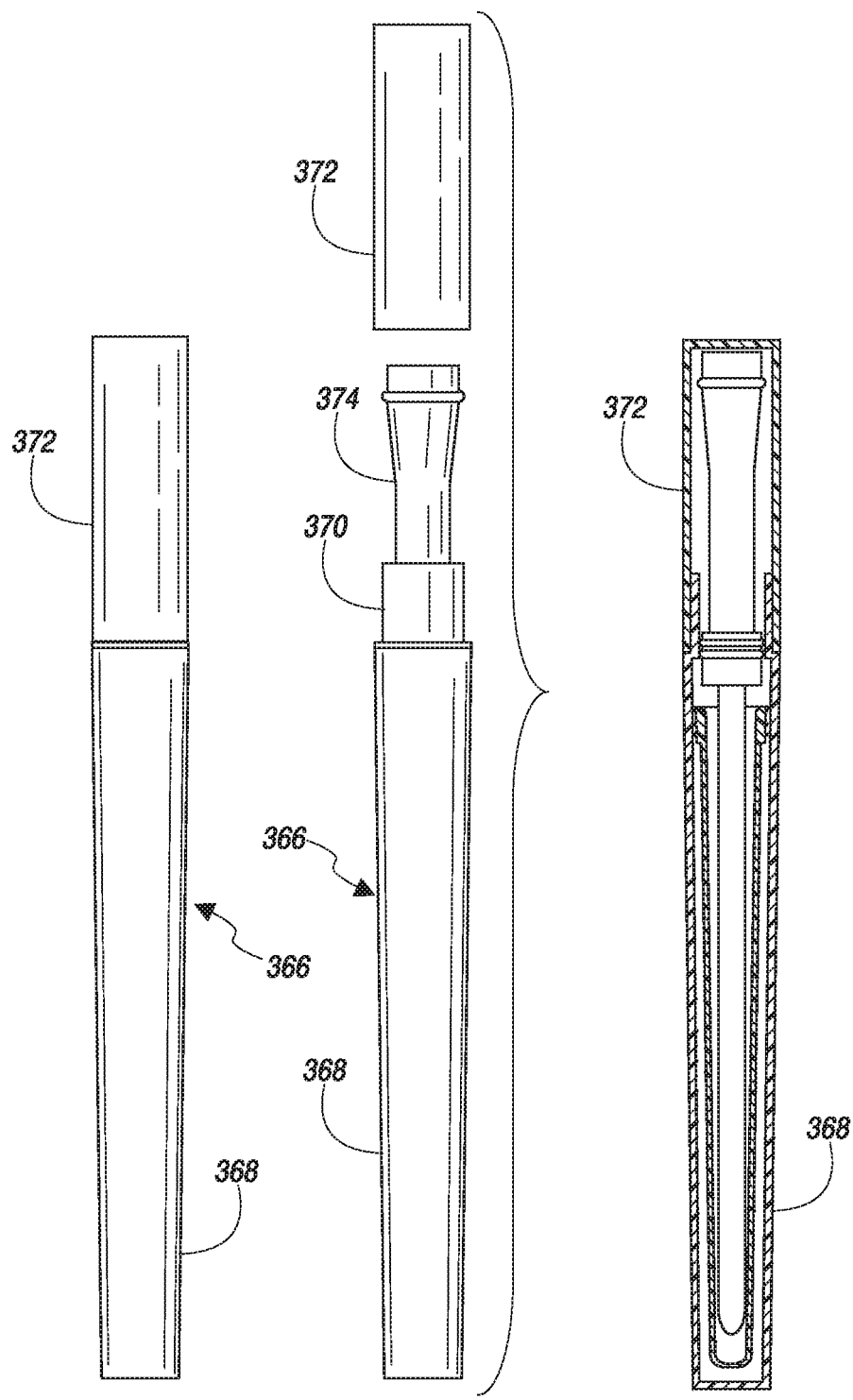
FIG. 53 is a side elevation view of an alternate embodiment of a catheter package assembly utilizing the hydration system of FIGS. 30-35.
FIG. 54 is an exploded view of the catheter package assembly of FIG. 53 with the cap removed to expose the funnel of the catheter.
FIG. 55 is a longitudinal section through the catheter package assembly of FIG. 53.

A liner hydrating mechanism similar to that shown in FIGS. 30-35 is incorporated in an alternate embodiment of a package, as shown in FIGS. 53-55. This catheter packaging assembly 366 includes a case 368. The case is hollow and has a ferrule 370 of reduced outside diameter at its open end. The ferrule may have an outwardly facing groove for receiving an O-ring (not shown). A cap 372 is an elongated hollow member having an inside diameter that allows it to just fit over the ferrule 370, with an interference fit with the O-ring providing a seal between the cap 372 and the case 368. The cap 372 also has sufficient height to permit the cap to enclose a funnel 374 of a catheter while engaging the ferrule 370. Inside the case 368 there is a liner 376 (FIG. 55) similar to the liner 252. As in the FIG. 30-35 embodiment, the liner has hydration windows covered by a patch of water vapor permeable material. This allows hydration of a catheter by placing liquid water in the case prior to installation of the liner. The liner prevents direct contact between the liquid water and the coating on the catheter's tubing but permits water vapor to keep the coating in condition where the catheter is ready to use when withdrawn from the case.

It should be understood that various changes and modifications to the presently preferred embodiments described herein will be apparent to those skilled in the art. Such changes and modifications can be made without departing from the spirit and scope of the invention disclosed herein. For example, while various O-rings are shown and described as separate, elastomeric rings, they could be molded as an integral part of the component. It is also pointed out that features described in connection with certain figures and embodiments are not limited to those specific embodiments. For example, funnel shapes and/or surfaces can be used with any of the embodiments described above. Similarly, hydrating elements, such as the liner described above, may be used with any one of the various package embodiments shown.

The invention claimed is:

1. A package for a medical device, the medical device having first and second portions, comprising:
   an elongated case defining an axis and having a rim defining an open end, the rim being sized to permit passage of the first portion of the medical device through said open end and into the elongated case which is sized to removably receive therein said first portion of the medical device, the rim being sized to prevent passage of the second portion of the medical device through said open end;
   a strap connected to the elongated case; and
   a cap connected to the strap and releasably engageable with the second portion of a medical device whose first portion has been inserted into the elongated case.

2. The package of claim 1 wherein the elongated case comprises a tubular wall.

3. The package of claim 2 further comprising a bottom wall attached to one end of the tubular wall.

4. The package of claim 2 wherein one end of the tubular wall has a tapered section terminating at the rim.

5. The package of claim 1 further comprising a boss formed on an underside of the cap.

6. The package of claim 5 wherein the boss has a rounded edge.

7. A catheter and package assembly, comprising:
   a catheter having an elongated tubing and a funnel attached to one end of the elongated tubing, the funnel having a seal portion and a body portion terminating at a free end;
   an elongated case defining an axis and having a rim defining an open end, the rim being sized to permit entry of the elongated tubing and the funnel seal portion through said open end and into the elongated case which is sized to removably receive therein the elongated tubing of the catheter, the rim being sized to prevent passage of the funnel body portion through said open end, the elongated case being releasably engageable by the seal portion of the funnel;
   a strap connected to the elongated case; and
   a cap connected to the strap and releasably engageable with the body portion of a funnel whose seal portion has been inserted into the elongated case.

8. The package assembly of claim 7 wherein the elongated case comprises a tubular wall.

9. The package assembly of claim 8 further comprising a bottom wall attached to one end of the tubular wall.

10. The package assembly of claim 8 wherein one end of the tubular wall has a tapered section terminating at the rim.

11. The package assembly of claim 7 further comprising a boss formed on an underside of the cap.

12. The package assembly of claim 11 wherein the boss has a rounded edge.

13. The package assembly of claim 7 wherein the elongated case has a seal face on its interior near the rim and the seal portion of the funnel is releasably engageable with the seal face.

14. The package assembly of claim 7 wherein the funnel body portion has a seal face on its interior near the free end and the cap is releasably engageable with the seal face at the free end of the body portion of the funnel.

15. The package assembly of claim 7 wherein the strap is initially disposed generally parallel to the axis of the elongated case.

16. The package assembly of claim 7 wherein the strap is initially disposed generally perpendicular to the axis of the elongated case.

17. The package assembly of claim 7 wherein the free end of the funnel defines an opening and the cap has a boss formed on an underside thereof, the boss sized to fit into the opening of the funnel.

18. The package assembly of claim 17 wherein the boss is spaced from the strap to permit the funnel to fit between the boss and the strap.

19. The package assembly of claim 7 wherein the seal portion of the funnel includes a compressible bead.

20. A catheter and package assembly, comprising:

a catheter having an elongated tubing and a funnel attached to one end of the elongated tubing, the funnel having a seal portion and a body portion terminating at a free end;

an elongated case defining an axis and having a rim defining an open end, the rim being sized to permit entry of the elongated tubing and the funnel seal portion through said open end and into the elongated case which is sized to removably receive therein the elongated tubing of the catheter, the rim being sized to prevent passage of the funnel body portion through said open end, the elongated case being releasably engageable by the seal portion of the funnel;

a cap releasably engageable with the body portion of a funnel whose seal portion has been inserted into the elongated case; and a strap connected to the elongated case, the cap being connected to the strap.

* * * * *